US012788925B2

(12) United States Patent
Goldspink

(10) Patent No.: US 12,788,925 B2
(45) Date of Patent: Nov. 10, 2026

(54) ADJUSTABLE POSITIONING AND STABILISING STRUCTURE

(71) Applicant: RESMED PTY LTD, Bella Vista (AU)

(72) Inventor: Lachlan Richard Goldspink, New South Wales (AU)

(73) Assignee: ResMed Pty Ltd, Bella Vista (AU)

( * ) Notice: Subject to any disclaimer, the term of this patent is extended or adjusted under 35 U.S.C. 154(b) by 835 days.

(21) Appl. No.: 18/017,391

(22) PCT Filed: Jul. 22, 2021

(86) PCT No.: PCT/AU2021/050786
§ 371 (c)(1),
(2) Date: Jan. 20, 2023

(87) PCT Pub. No.: WO2022/016220
PCT Pub. Date: Jan. 27, 2022

(65) Prior Publication Data

US 2023/0285705 A1 Sep. 14, 2023

(30) Foreign Application Priority Data

Jul. 22, 2020 (AU) ................................ 2020902538

(51) Int. Cl.
*A61M 16/06* (2006.01)
*A61M 16/08* (2006.01)

(52) U.S. Cl.
CPC .... *A61M 16/0683* (2013.01); *A61M 16/0616* (2014.02); *A61M 16/0875* (2013.01)

(58) Field of Classification Search
CPC .......... A61M 16/0616; A61M 16/0683; A61M 16/0875
See application file for complete search history.

(56) References Cited

U.S. PATENT DOCUMENTS 4,782,832 A 11/1988 Trimble et al.
6,581,594 B1 6/2003 Drew et al.
(Continued)

FOREIGN PATENT DOCUMENTS

WO WO 1998/004310 A1 2/1998
WO WO 1998/034665 A1 8/1998
(Continued)

OTHER PUBLICATIONS

International Search Report dated Oct. 12, 2021 issued in International Application No. PCT/AU2021/050786 (7 pages).
(Continued)

*Primary Examiner* — Valerie L Woodward
(74) *Attorney, Agent, or Firm* — Nixon & Vanderhye P.C.

(57) ABSTRACT

A positioning and stabilising structure comprises a gas delivery tube to receive a flow of air from a connection port on top of the patient's head and to deliver the flow of air to the entrance of the patient's airways via the seal-forming structure. The gas delivery tube has a first portion, a second portion, and a variable length portion which is extendible and/or compressible. The positioning and stabilising structure further comprises an adjustment means which is attached or attachable to the first portion of the gas delivery tube and is attached or attachable to the second portion of the gas delivery tube. The connection between the adjustment means and the gas delivery tube can be varied to thereby adjust the length of the variable length portion and/or the length of the adjustment means is selectively adjustable to thereby adjust the length of the variable length portion.

18 Claims, 36 Drawing Sheets

(56) References Cited

U.S. PATENT DOCUMENTS

| | | | | |
|---|---|---|---|---|
| 7,735,490 | B2 | 6/2010 | Rinaldi | |
| 2009/0044808 | A1 | 2/2009 | Guney et al. | |
| 2009/0050156 | A1 | 2/2009 | Ng et al. | |
| 2010/0000534 | A1 | 1/2010 | Kooij et al. | |
| 2011/0197341 | A1* | 8/2011 | Formica | B32B 5/024 2/209.3 |
| 2012/0325219 | A1 | 12/2012 | Smith | |
| 2013/0220327 | A1* | 8/2013 | Barlow | A61M 16/0816 128/205.25 |
| 2017/0182276 | A1* | 6/2017 | Hammer | A62B 18/084 |
| 2018/0214656 | A1* | 8/2018 | McLaren | A61M 16/06 |
| 2019/0022343 | A1* | 1/2019 | Kooij | A61M 16/06 |
| 2019/0111227 | A1 | 4/2019 | Veliss et al. | |

FOREIGN PATENT DOCUMENTS

| | | | | |
|---|---|---|---|---|
| WO | WO 2000/078381 | A1 | 12/2000 | |
| WO | WO 2004/073778 | A1 | 9/2004 | |
| WO | WO 2005/063328 | A1 | 7/2005 | |
| WO | WO 2006/074513 | A1 | 7/2006 | |
| WO | WO 2006/130903 | A1 | 12/2006 | |
| WO | WO-2009052560 | A1 * | 4/2009 | A61M 16/0683 |
| WO | WO 2010/135785 | A1 | 12/2010 | |
| WO | WO 2016/193859 | A1 | 12/2016 | |
| WO | WO 2019/185474 | A1 | 10/2019 | |

OTHER PUBLICATIONS

Written Opinion of the International Searching Authority dated Oct. 12, 2021 issued in International Application No. PCT/AU2021/050786 (6 pages).

* cited by examiner

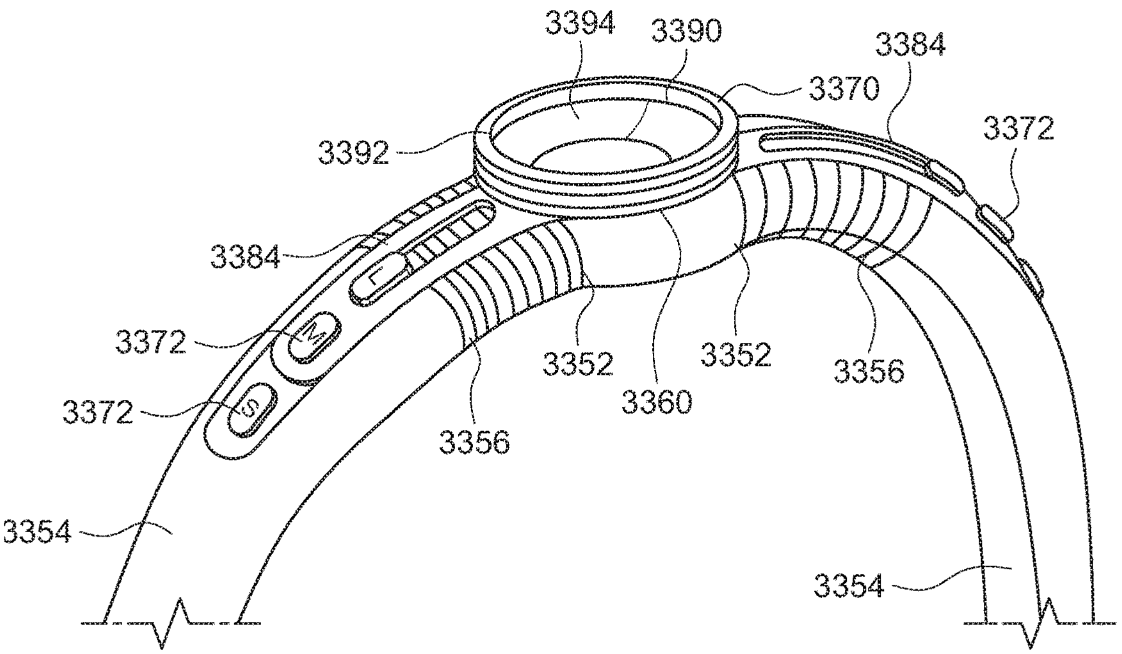
FIG. 10
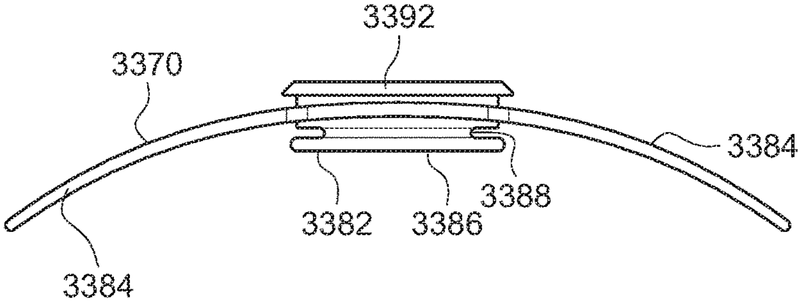
FIG. 11
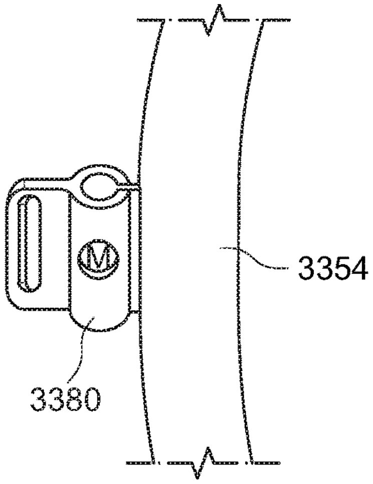
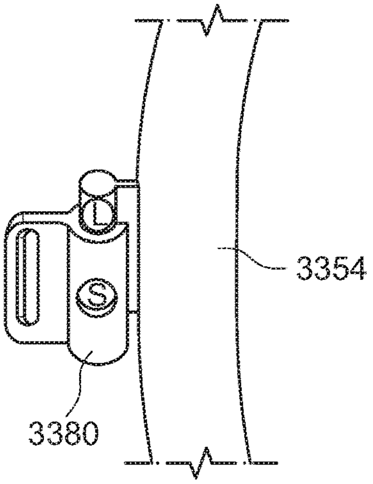
FIG. 12A FIG. 12B

Fig. 27A
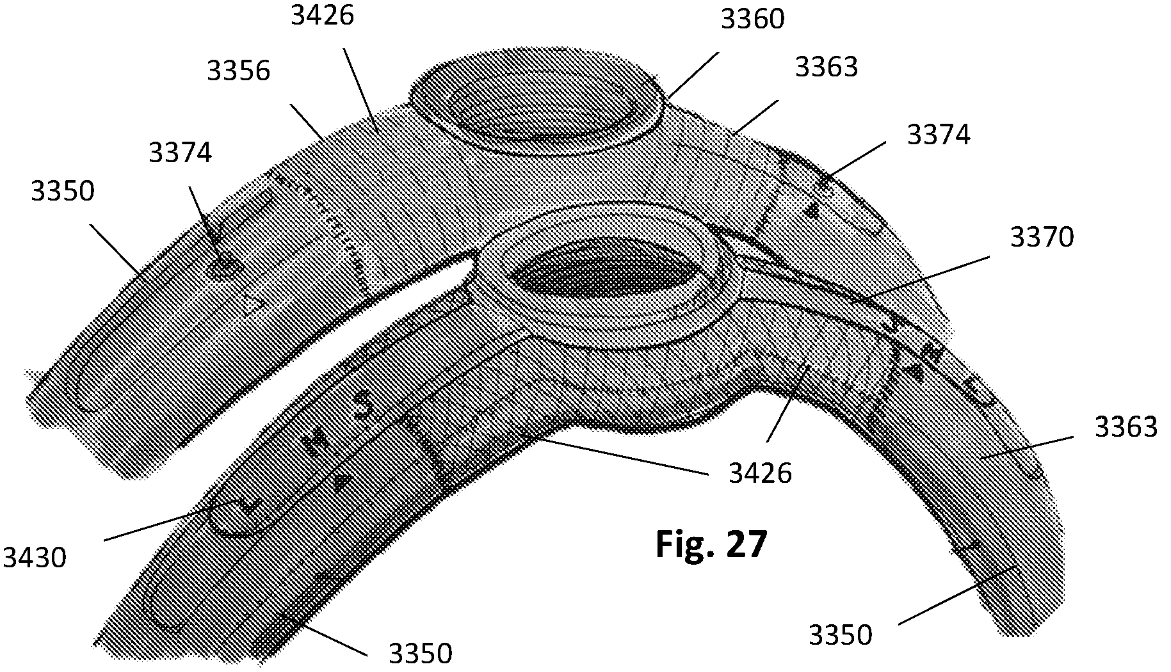
Fig. 27
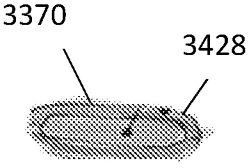
Fig. 27C
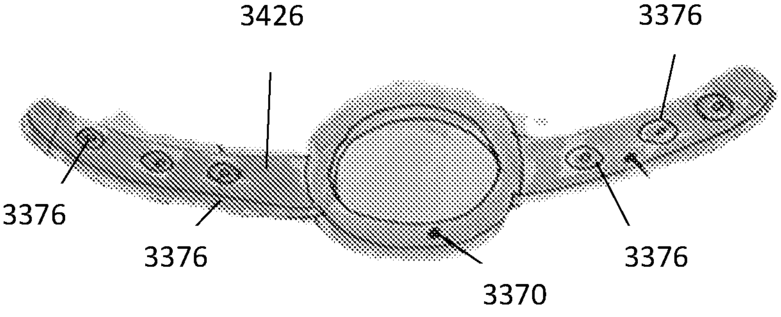
Fig. 27B

ADJUSTABLE POSITIONING AND STABILISING STRUCTURE

CROSS-REFERENCE TO RELATED APPLICATIONS

This application is the U.S. national phase of International Application No. PCT/AU2021/050786 filed Jul. 22, 2021 which designated the U.S. and claims priority to AU 2020902538 filed Jul. 22, 2020, the entire contents of each of which are hereby incorporated by reference.

1 BACKGROUND OF THE TECHNOLOGY

1.1 Field of the Technology

The present technology relates to one or more of the screening, diagnosis, monitoring, treatment, prevention and amelioration of respiratory-related disorders. The present technology also relates to medical devices or apparatus, and their use.

1.2 Description of the Related Art 1.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

1.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

1.2.2.1 Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

1.2.2.2 Flow Therapies

Not all respiratory therapies aim to deliver a prescribed therapeutic pressure. Some respiratory therapies aim to deliver a prescribed respiratory volume, by delivering an inspiratory flow rate profile over a targeted duration, possibly superimposed on a positive baseline pressure. In other cases, the interface to the patient's airways is 'open' (unsealed) and the respiratory therapy may only supplement the patient's own spontaneous breathing with a flow of conditioned or enriched gas. In one example, High Flow therapy (HFT) is the provision of a continuous, heated, humidified flow of air to an entrance to the airway through an unsealed or open patient interface at a "treatment flow rate" that is held approximately constant throughout the respiratory cycle. The treatment flow rate is nominally set to exceed the patient's peak inspiratory flow rate. HFT has been used to treat OSA, CSR, respiratory failure, COPD, and other respiratory disorders. One mechanism of action is that the high flow rate of air at the airway entrance improves ventilation efficiency by flushing, or washing out, expired $CO_2$ from the patient's anatomical deadspace. Hence, HFT is thus sometimes referred to as a deadspace therapy (DST). Other benefits may include the elevated warmth and humidification (possibly of benefit in secretion management) and the potential for modest elevation of airway pressures. As an alternative to constant flow rate, the treatment flow rate may follow a profile that varies over the respiratory cycle.

Another form of flow therapy is long-term oxygen therapy (LTOT) or supplemental oxygen therapy. Doctors may prescribe a continuous flow of oxygen enriched gas at a specified oxygen concentration (from 21%, the oxygen fraction in ambient air, to 100%) at a specified flow rate (e.g., 1 litre per minute (LPM), 2 LPM, 3 LPM, etc.) to be delivered to the patient's airway.

1.2.2.3 Supplementary Oxygen

For certain patients, oxygen therapy may be combined with a respiratory pressure therapy or HFT by adding supplementary oxygen to the pressurised flow of air. When oxygen is added to respiratory pressure therapy, this is referred to as RPT with supplementary oxygen. When oxygen is added to HFT, the resulting therapy is referred to as HFT with supplementary oxygen.

1.2.3 Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

Another form of therapy system is a mandibular repositioning device.

1.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$. For flow therapies such as nasal HFT, the patient interface is configured to insufflate the nares but specifically to avoid a complete seal. One example of such a patient interface is a nasal cannula.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

1.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

1.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

Positioning and stabilising structures often comprise at least one strap that is extensible, e.g. resiliently extensible. For example the strap may be configured in use to be in tension, and to direct a force to draw a seal-forming structure into sealing contact with a portion of a patient's face. Other forms of positioning and stabilising structure rely on conduits to provide the force which draws the seal-forming structure into contact with the patient's face. While such conduits may also comprise resiliently extensible portions, the ability of such "conduit headgear" to extend sufficiently to suit patients with large heads, while still providing sufficient interfacing force when used by patient with small heads, is limited. Accordingly, manufacturers typically make at least two different sizes of conduit headgear in order to adequately meet the needs of different sized patients.

Making different sizes of such headgear may be inefficient from a manufacturing and supply point of view, and also increases the chance that a patient will be provided with the wrong size headgear.

Conduit headgear is often provided with means for attaching a back strap to the conduits. Correctly positioning the connection of the back strap to the conduit is important for maintaining the correct sealing force. However, changes in length of the conduit may result in the back strap connection being positioned incorrectly relative to the patient's head or airways.

1.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include a CPAP device and a ventilator.

1.2.3.3 Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

1.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. Humidifiers therefore often have the capacity to heat the flow of air was well as humidifying it.

1.2.3.5 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

1.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focused airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

1.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

2 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

One form of the present technology comprises a positioning and stabilising structure to provide a force to hold a seal-forming structure in a therapeutically effective position on a patient's head, the seal-forming structure constructed and arranged to form a seal with a region of the patient's face surrounding an entrance to the patient's airways for sealed delivery of a flow of air at a therapeutic pressure of at least 6 cmH2O above ambient air pressure to at least the patient's nares throughout the patient's respiratory cycle in use, the positioning and stabilising structure comprising:

- a gas delivery tube to receive the flow of air from a connection port on top of the patient's head and to deliver the flow of air to the entrance of the patient's airways via the seal-forming structure, the gas delivery tube being constructed and arranged to contact, in use, at least a region of the patient's head superior to an otobasion superior of the patient's head,
- the gas delivery tube further comprising a first portion, a second portion, and a variable length portion between the first and second portions which is extendible and/or compressible,
- the positioning and stabilising structure further comprising an adjustment means which is attached or attachable to the first portion of the gas delivery tube and is attached or attachable to the second portion of the gas delivery tube, wherein the connection between the adjustment means and the gas delivery tube can be varied to thereby adjust the length of the variable length portion and/or the length of the adjustment means is selectively adjustable to thereby adjust the length of the variable length portion.

Another form of the present technology comprises a positioning and stabilising structure to provide a force to hold a seal-forming structure in a therapeutically effective position on a patient's head, the seal-forming structure constructed and arranged to form a seal with a region of the patient's face surrounding an entrance to the patient's airways for sealed delivery of a flow of air at a therapeutic pressure of at least 6 cmH2O above ambient air pressure to at least the patient's nares throughout the patient's respiratory cycle in use, the positioning and stabilising structure comprising:

- a gas delivery tube to receive the flow of air from a connection port on top of the patient's head and to deliver the flow of air to the entrance of the patient's airways via the seal-forming structure, the gas delivery tube being constructed and arranged to contact, in use, at least a region of the patient's head superior to an otobasion superior of the patient's head,
- the gas delivery tube further comprising a first portion, a second portion, and a variable length portion between the first and second portions which is extendible and/or compressible, wherein the second portion comprises a plurality of spaced apart attachment means,
- the positioning and stabilising structure further comprising an adjustment member which is attached or attachable to the first portion of the gas delivery tube and is attachable to a selected one of the attachment means to thereby adjust the length of the variable length portion.

In examples:

a) each attachment means comprises a projecting portion adapted to engage an aperture in the adjustment member;
b) the attachment means comprise mushroom connectors;
c) an aperture is provided at each end of the adjustment member;
d) the or each tube comprises a rib extending from a posterior surface thereof, wherein the attachment means project from a surface of the rib;
e) the attachment means extend laterally from a lateral surface of the rib;
f) the adjustment member extends, in use, over the top of the patient's head;
g) the positioning and stabilising structure comprises a second gas delivery tube and the adjustment member is attachable to the attachment means of both tubes;
h) the positioning and stabilising structure comprises a fluid connection opening and the adjustment member comprises a cylindrical portion which engages the opening, wherein a bore extends through the cylindrical portion to the opposite side of the attachment member;
i) the bore comprises a formation configured to engage an elbow;
j) strap engaging portions are provided to the or each tube;
j) each strap engaging portion is slideable relative to the tube;
j) the adjustment member is provided with a strap engaging portion;
k) the strap engaging portion is located at a centre of the adjustment member;
l) the strap engaging portion is located at one end of the adjustment member;
m) the attachment portions are configured to allow adjustment of the length of the tube in 30 mm increments; and/or
n) each tube portion is provided with three attachment portions.

Another form of the present technology comprises a positioning and stabilising structure to provide a force to hold a seal-forming structure in a therapeutically effective position on a patient's head, the seal-forming structure constructed and arranged to form a seal with a region of the patient's face surrounding an entrance to the patient's airways for sealed delivery of a flow of air at a therapeutic pressure of at least 6 cmH2O above ambient air pressure to at least the patient's nares throughout the patient's respiratory cycle in use, the positioning and stabilising structure comprising:

a gas delivery tube to receive the flow of air from a connection port on top of the patient's head and to deliver the flow of air to the entrance of the patient's airways via the seal-forming structure, the gas delivery tube being constructed and arranged to contact, in use, at least a region of the patient's head superior to an otobasion superior of the patient's head, the gas delivery tube further comprising a first portion, a second portion, and a variable length portion between the first and second portions which is extendible and/or compressible, the second portion comprising an attachment means, the positioning and stabilising structure further comprising an adjustment member which is attached or attachable to the first portion of the gas delivery tube and is attachable to the attachment means at a selected one of a plurality of locations along the adjustment member to thereby adjust the length of the variable length portion.

In examples:

a) the adjustment member is configured to remain connected to the tube while the length of the tube is adjusted;
b) an attachment means is provided to the variable length portion;
c) attachment means are provided to the posterior of tube; and/or
d) the adjustment member comprises a strap engaging portion.

Another form of the present technology comprises a positioning and stabilising structure to provide a force to hold a seal-forming structure in a therapeutically effective position on a patient's head, the seal-forming structure constructed and arranged to form a seal with a region of the patient's face surrounding an entrance to the patient's airways for sealed delivery of a flow of air at a therapeutic pressure of at least 6 cmH2O above ambient air pressure to at least the patient's nares throughout the patient's respiratory cycle in use, the positioning and stabilising structure comprising:

a gas delivery tube to receive the flow of air from a connection port on top of the patient's head and to deliver the flow of air to the entrance of the patient's airways via the seal-forming structure, the gas delivery tube being constructed and arranged to contact, in use, at least a region of the patient's head superior to an otobasion superior of the patient's head, the gas delivery tube further comprising a first portion, a second portion, and a variable length portion between the first and second portions which is extendible and/or compressible, the positioning and stabilising structure further comprising an adjustment member which is connected to the first portion of the gas delivery tube and to the second portion of the gas delivery tube, wherein the connection between the adjustment member and at least one of the first and second portions of the gas delivery tube is slideable to allow adjustment of the length of the variable length portion, wherein the or each slideable connection is configured to resist sliding when in at least one position.

In examples:

a) each of the first and second portions is provided with an elongate rail portion which is substantially parallel to the longitudinal axis of the tube;
b) the elongate rail portions are provided to the posterior of the tube;
c) the adjustment member comprises a rail engaging portion;
d) the rail engaging portion comprises a channel;
e) the channel has a substantially circular cross section;
f) the rail engaging portion is a tight sliding fit on a least one portion of the rail portion;
g) the rail portion comprises a detent formation;
h) the adjustment member is connected to the variable length portion;
i) the connection between the rail engaging portion and the rail portion is configured to resist bending; and/or
j) the adjustment member comprises a strap engaging portion.

Another form of the present technology comprises a positioning and stabilising structure to provide a force to hold a seal-forming structure in a therapeutically effective position on a patient's head, the seal-forming structure constructed and arranged to form a seal with a region of the patient's face surrounding an entrance to the patient's airways for sealed delivery of a flow of air at a therapeutic pressure of at least 6 cmH2O above ambient air pressure to at least the patient's nares throughout the patient's respiratory cycle in use, the positioning and stabilising structure comprising:

a gas delivery tube to receive the flow of air from a connection port on top of the patient's head and to deliver the flow of air to the entrance of the patient's airways via the seal-forming structure, the gas delivery tube being constructed and arranged to contact, in use, at least a region of the patient's head superior to an otobasion superior of the patient's head, the gas delivery tube further comprising a first portion, a second portion, and a variable length portion between the first and second portions which is extendible and/or compressible, the positioning and stabilising structure further comprising an adjustment means comprising a first adjustment means member connected to the first portion of the gas delivery tube and a second adjustment means member connected to the second portion of the gas delivery tube, wherein the first adjustment means member is slideably engaged with the second adjustment means member, wherein the slideable engagement is configured to resist sliding when the first adjustment means member is in at least one position relative to the second adjustment means member, and wherein sliding the first adjustment means member relative to the second adjustment means member adjusts the length of the adjustment means and the length of the variable length portion of the tube.

In examples:

a) the first adjustment means member comprises two substantially parallel leg portions and the second adjustment means member comprises two substantially parallel leg portions which are shaped and configured to receive the leg portions of the first adjustment means member;

b) the leg portions of the second adjustment means member are hollow so that the leg portions of the first adjustment means member can be received within the hollow portions of the legs of the second adjustment means member;

c) the second adjustment means member comprises a plurality of detent apertures, recesses or notches spaced along the second attachment member and the legs of the first adjustment means member are each provided with a detent button or projection which releasably engages a selected one of the detent apertures, recesses or notches.

e) a strap engaging portion is provided to the tube;

f) the strap engaging portions projects through the space between the spaced apart legs of the first and second attachment members; and/or g) the first adjustment means member is provided with markings which indicate the setting of the adjustment means, wherein the markings are arranged such that the marking corresponding to the current setting of the adjustment means is viewable through an aperture provided in the second adjustment means member.

Another form of the present technology comprises a system for positioning and stabilising a patient interface, the system comprising:

a positioning and stabilising structure to provide a force to hold a seal-forming structure in a therapeutically effective position on a patient's head, the seal-forming structure constructed and arranged to form a seal with a region of the patient's face surrounding an entrance to the patient's airways for sealed delivery of a flow of air at a therapeutic pressure of at least 6 cmH2O above ambient air pressure to at least the patient's nares throughout the patient's respiratory cycle in use, the positioning and stabilising structure comprising:

a gas delivery tube to receive the flow of air from a connection port on top of the patient's head and to deliver the flow of air to the entrance of the patient's airways via the seal-forming structure, the gas delivery tube being constructed and arranged to contact, in use, at least a region of the patient's head superior to an otobasion superior of the patient's head, the gas delivery tube further comprising a first portion, a second portion, and a variable length portion between the first and second portions which is extendible and/or compressible, each of the first and second portions comprising an attachment means, the system further comprising a plurality of adjustment members, wherein a length of each of the adjustment members is different to a length of each of the other adjustment members, wherein each of the adjustment members is configured to be attachable to the first portion of the gas delivery tube and the second portion of the gas delivery tube to thereby set the length of the variable length portion to a required length.

In examples:

a) the tube is substantially D shaped in cross-section;

b) the first and second portions of the tube comprise recessed portions immediately adjacent the variable length portion of the tube;

c) the attachment means are provided to each of the recessed portions, the attachment means configured to engage suitable recesses and/or apertures in the adjustment members;

d) each adjustment member may be provided with a strap engaging portion;

e) each adjustment member is substantially flat and thin, and the strap engaging portion is provided substantially in-plane with the remainder of the attachment member;

f) the attachment means have a non-circular cross-section;

g) the strap engaging portion is provided substantially centrally along the length of the adjustment member;

h) the strap engaging portion is provided at one end of the adjustment member; and/or j) each adjustment member is configured to be usable on either side of the patient's head.

Another form of the present technology comprises a positioning and stabilising structure to provide a force to hold a seal-forming structure in a therapeutically effective position on a patient's head, the seal-forming structure constructed and arranged to form a seal with a region of the patient's face surrounding an entrance to the patient's airways for sealed delivery of a flow of air at a therapeutic pressure of at least 6 cmH2O above ambient air pressure to at least the patient's nares to at least the patient's nares throughout the patient's respiratory cycle in use, the positioning and stabilising structure comprising:

a gas delivery tube to receive the flow of air from a connection port on top of the patient's head and to deliver the flow of air to the entrance of the patient's airways via the seal-forming structure, the gas delivery tube being constructed and arranged to contact, in use, at least a region of the patient's head superior to an otobasion superior of the patient's head, the gas delivery tube further comprising a first portion, a second portion, and a variable length portion between the first and second portions which is extendible and/or compressible, the second portion comprising an attachment means, the positioning and stabilising structure further comprising an adjustment member which is attachable to the first portion of the gas delivery tube and the second portion of the gas delivery tube to thereby set the length of the variable length portion to a required length.

Another aspect of one form of the present technology is a system for positioning and stabilising.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

3 BRIEF DESCRIPTION OF THE DRAWINGS

The present technology is illustrated by way of example, and not by way of limitation, in the figures of the accompanying drawings, in which like reference numerals refer to similar elements including:

3.1 Respiratory Therapy Systems

FIG. 1A shows a system including a patient 1000 wearing a patient interface 3000, in the form of nasal pillows, receiving a supply of air at positive pressure from an RPT device 4000. Air from the RPT device 4000 is conditioned in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

3.2 Respiratory System and Facial Anatomy

Figure 1A:
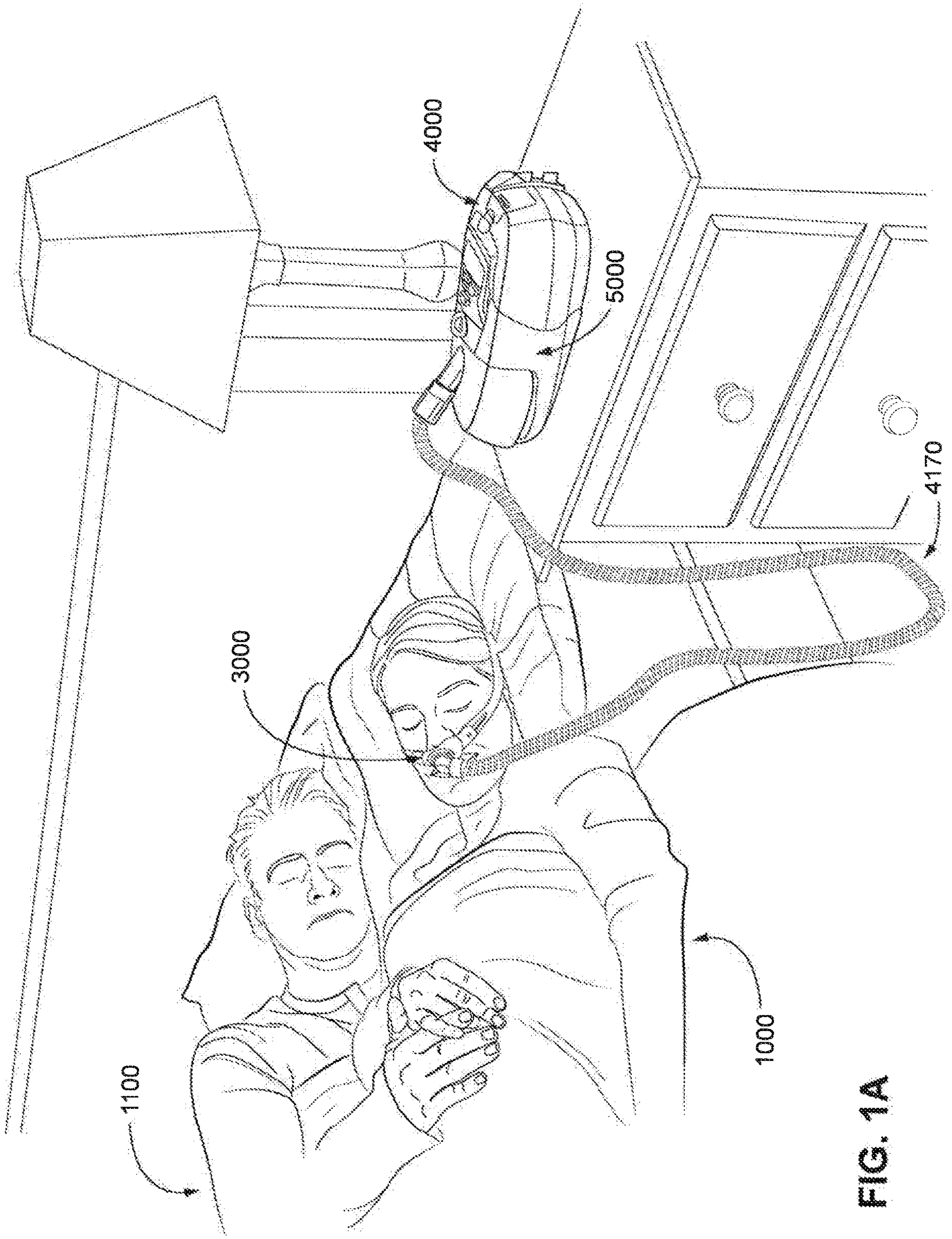
Figure 1B:
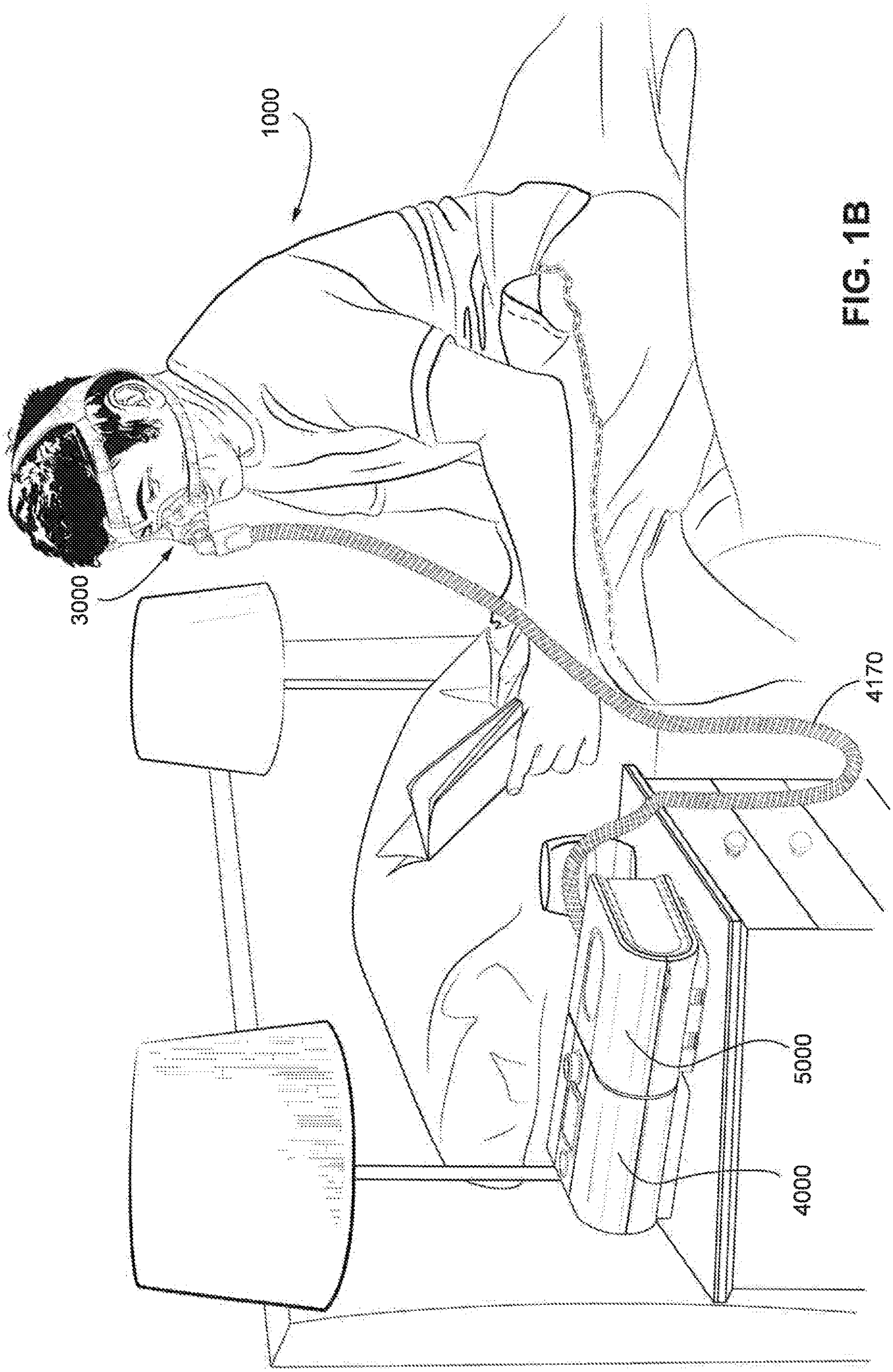
Figure 1C:
Figure 2A:
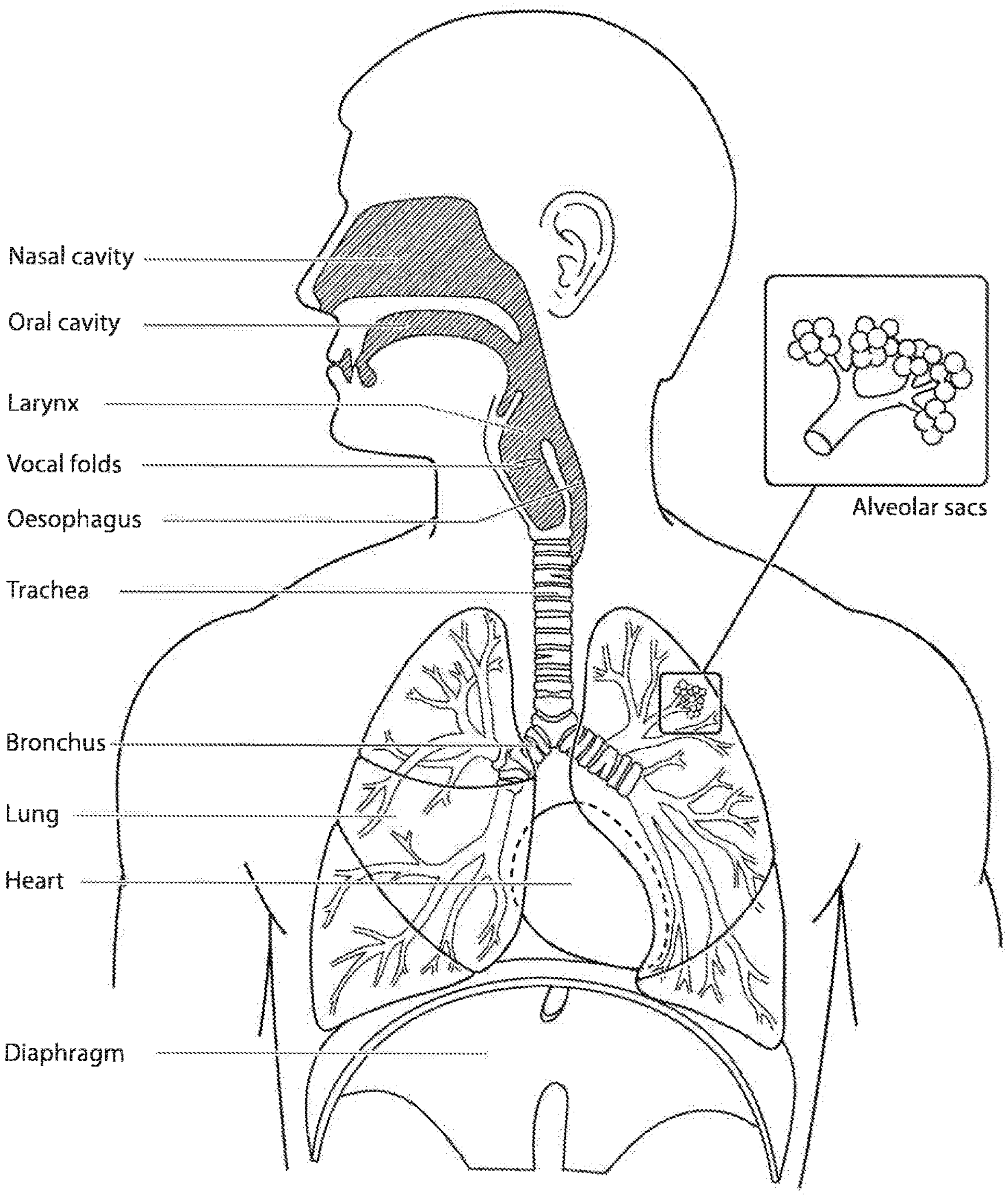
FIG. 2A shows an overview of a human respiratory system including the nasal and oral cavities, the larynx, vocal folds, oesophagus, trachea, bronchus, lung, alveolar sacs, heart and diaphragm.
Figure 2B:
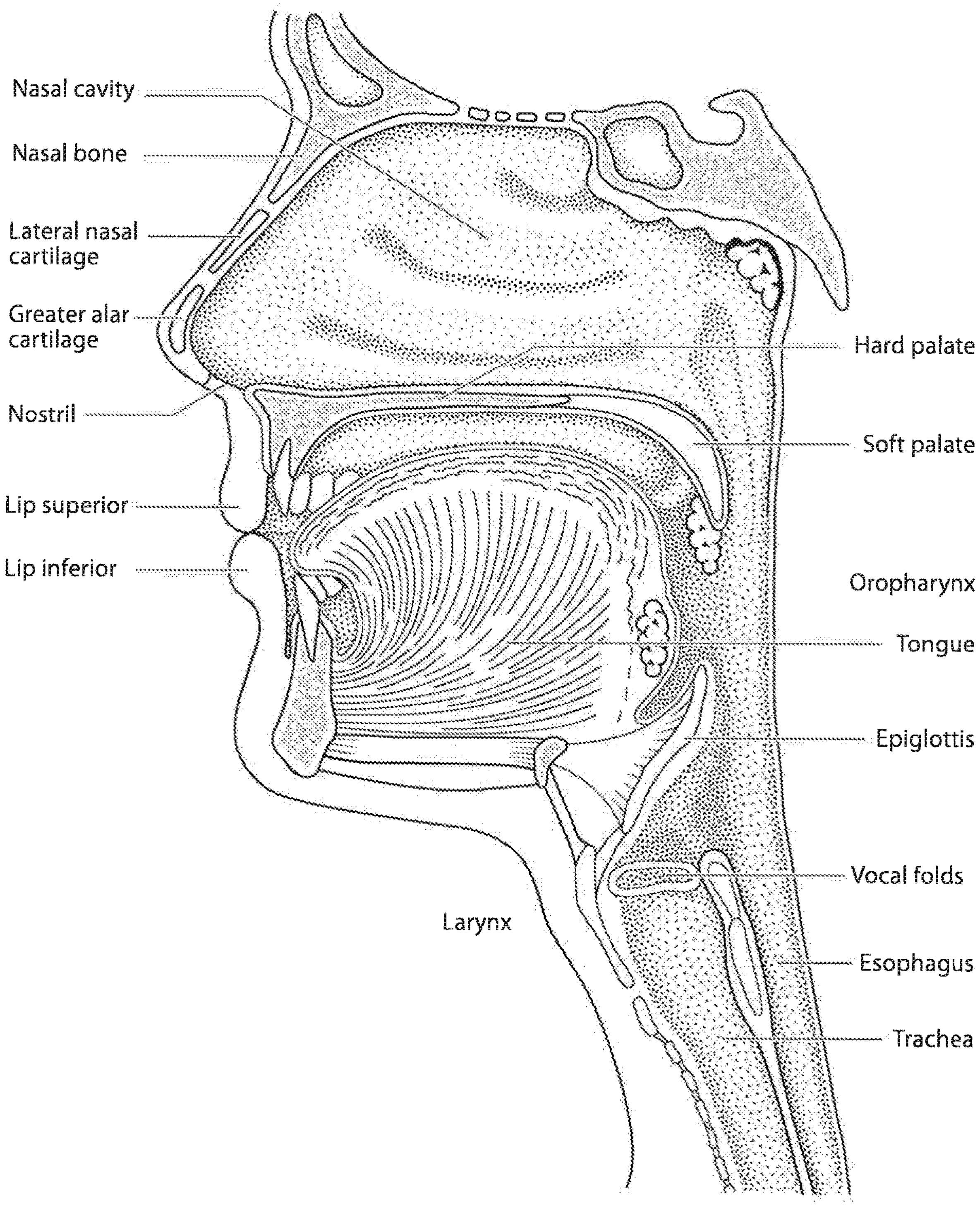
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
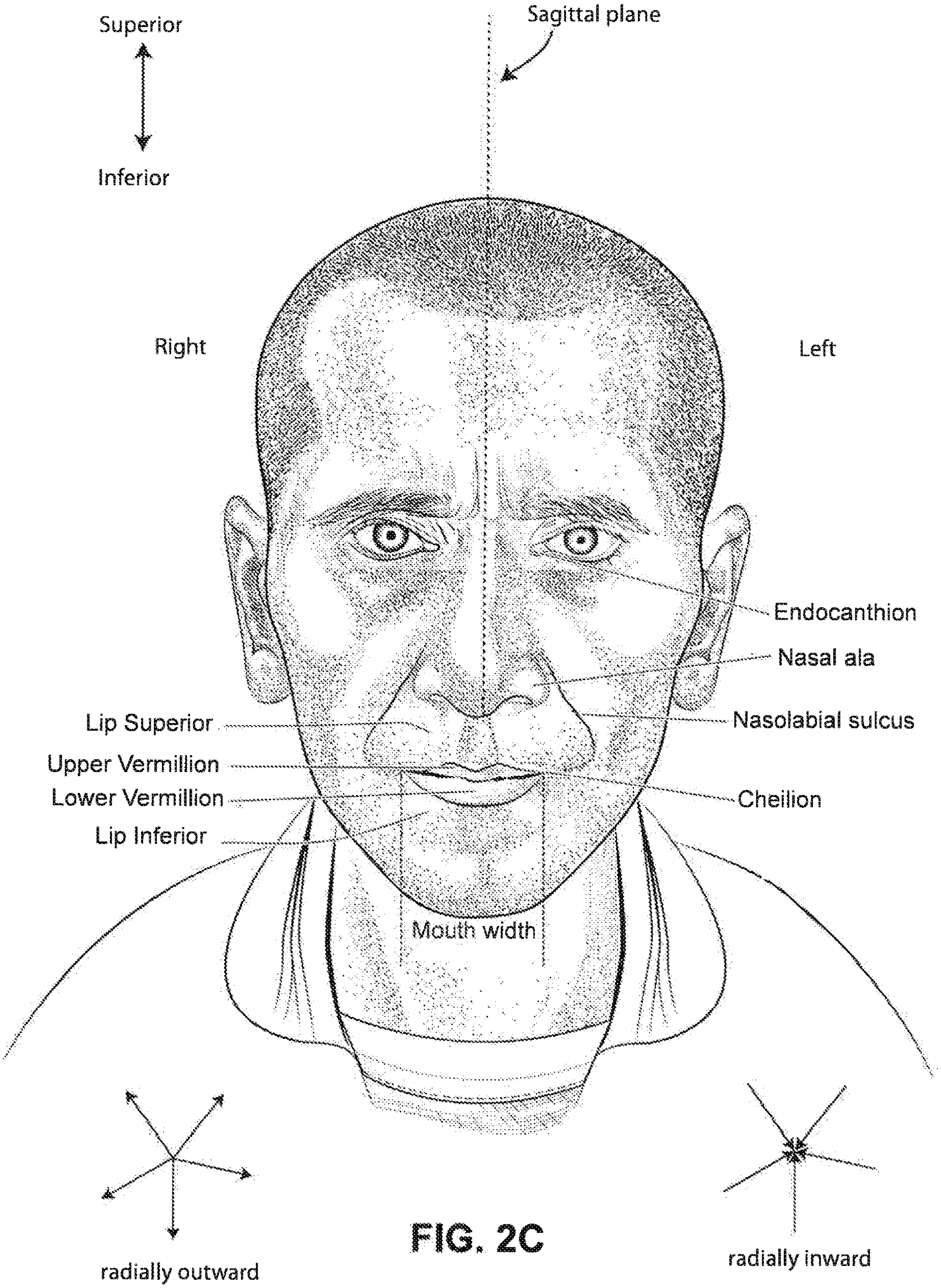
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
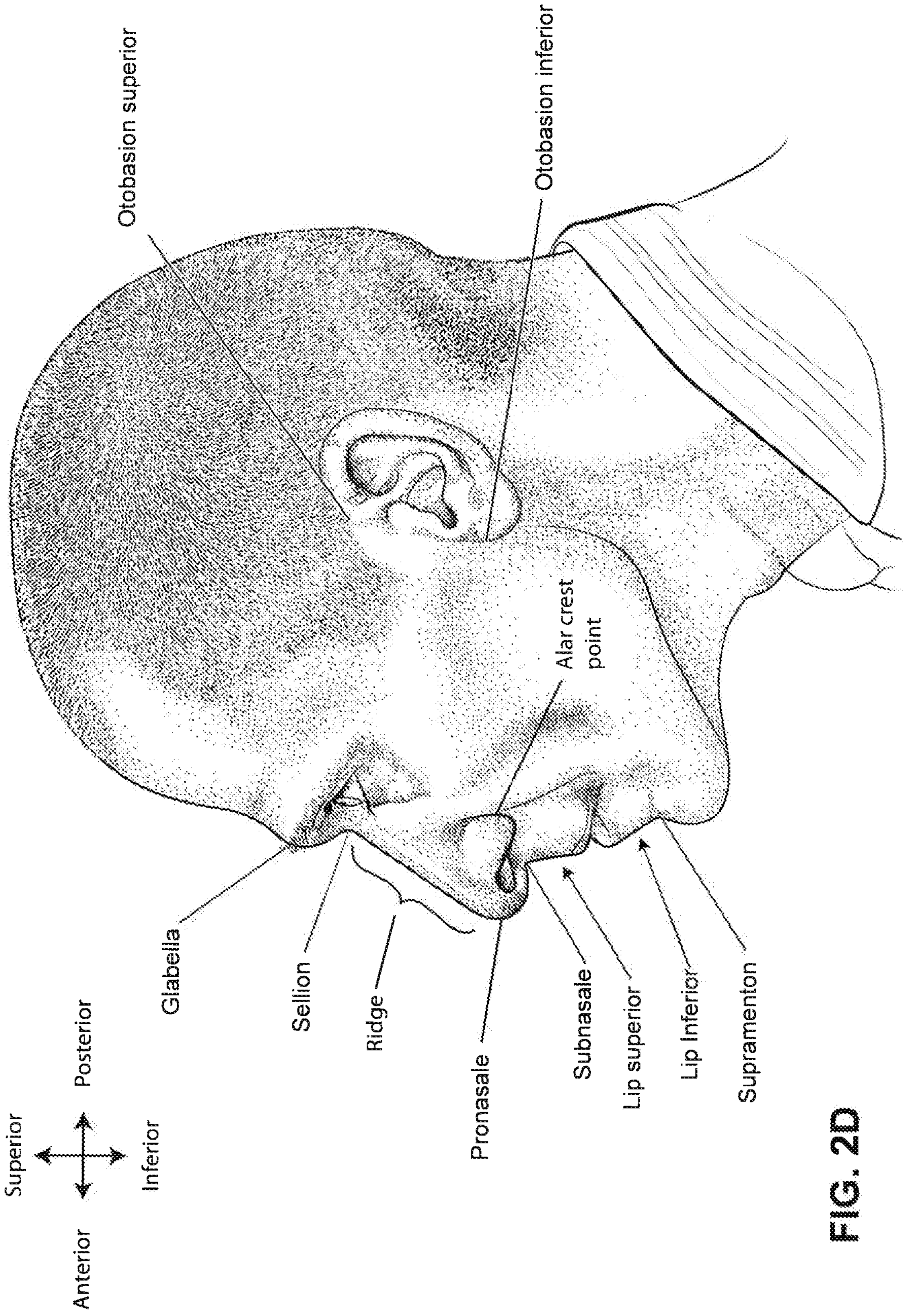
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
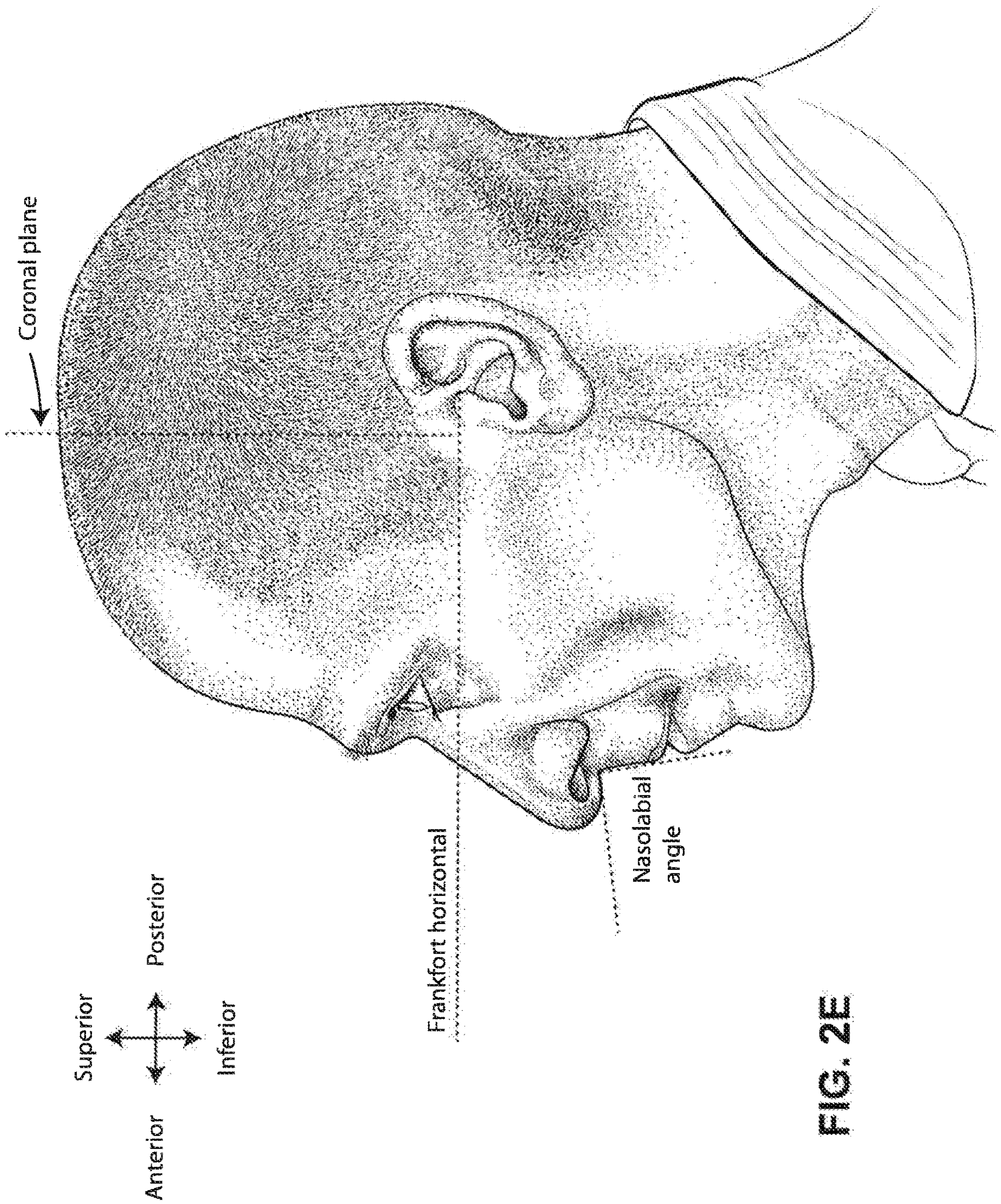

FIG. 2E is a further side view of a head. The approximate locations of the Frankfort horizontal and nasolabial angle are indicated. The coronal plane is also indicated.

Figure 2F:
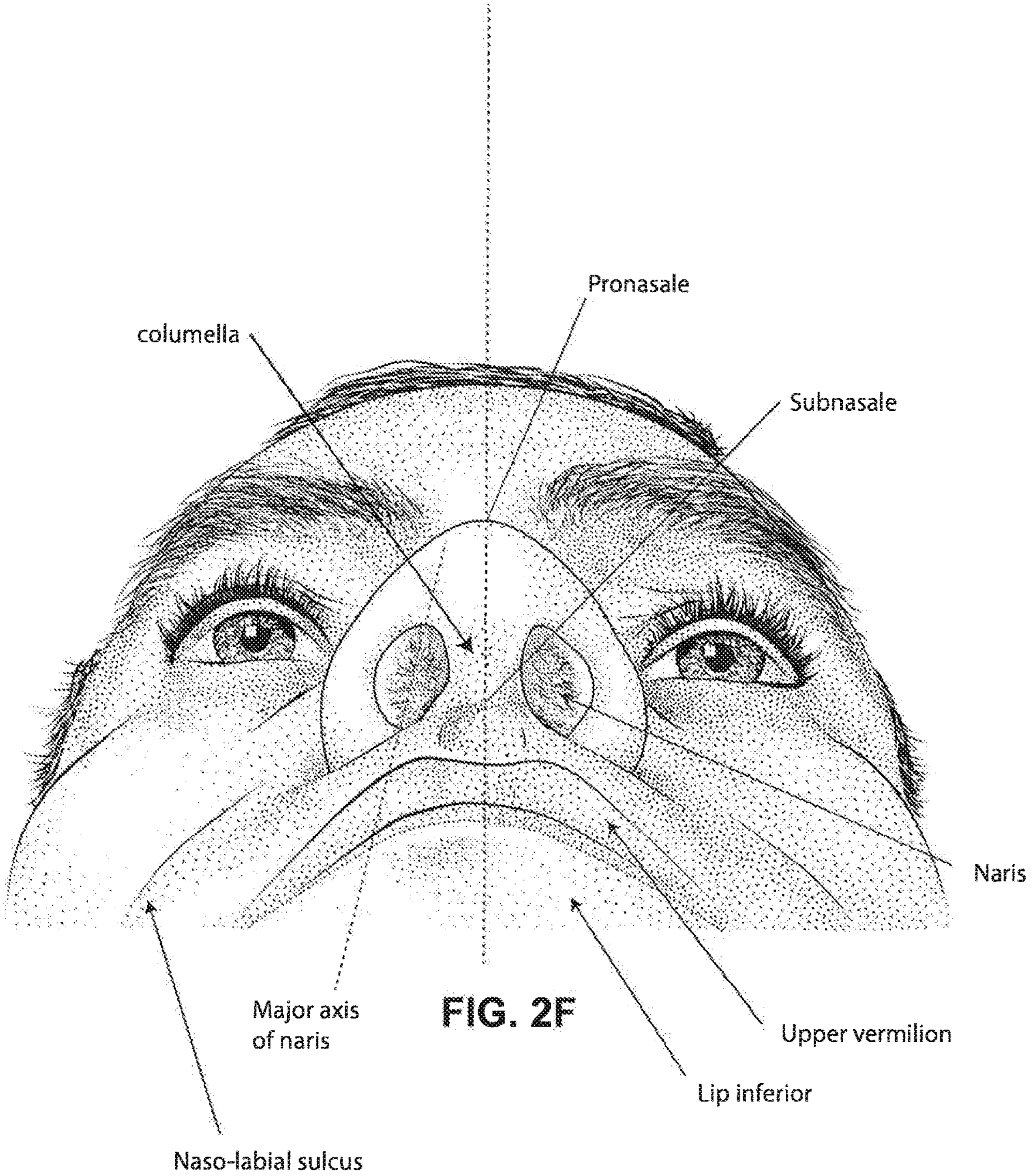

FIG. 2F shows a base view of a nose with several features identified including naso-labial sulcus, lip inferior, upper Vermilion, naris, subnasale, columella, pronasale, the major axis of a naris and the midsagittal plane.

Figure 2G:
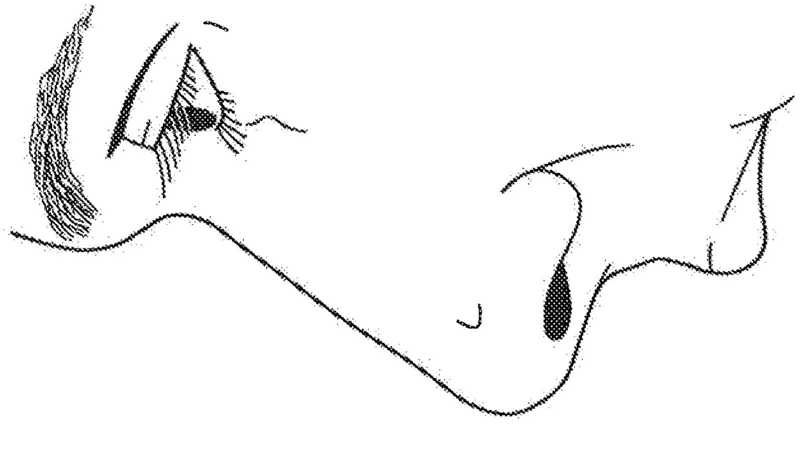

FIG. 2G shows a side view of the superficial features of a nose.

Figure 2H:
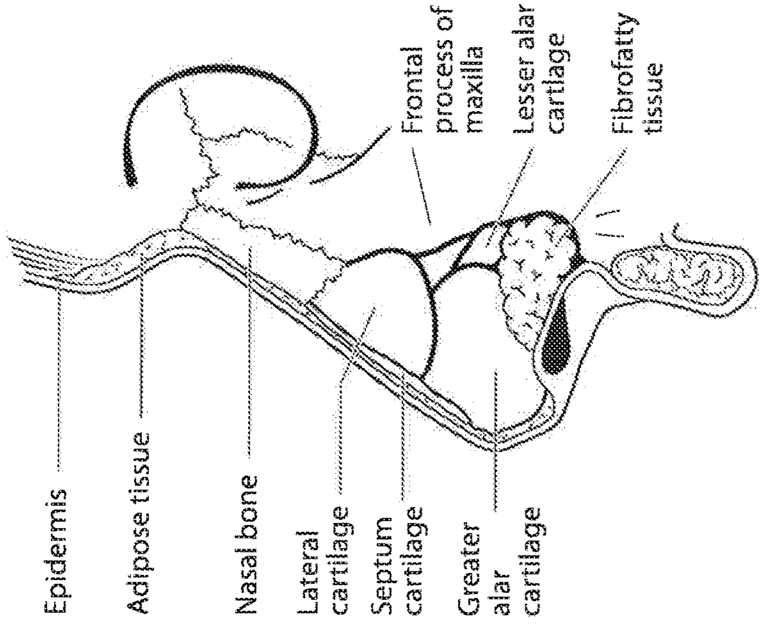

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

Figure 2I:
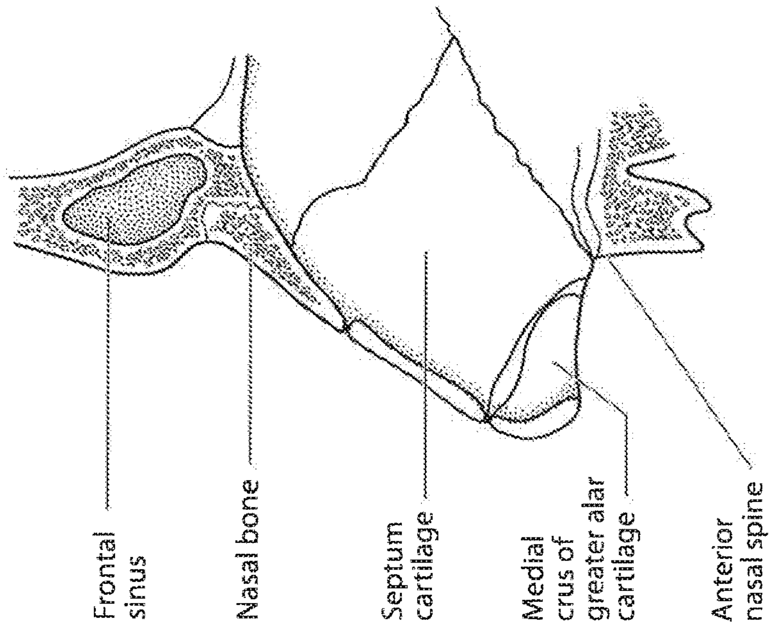

FIG. 2I shows a medial dissection of a nose, approximately several millimeters from the midsagittal plane, amongst other things showing the septum cartilage and medial crus of greater alar cartilage.

Figures 2J, 2K:
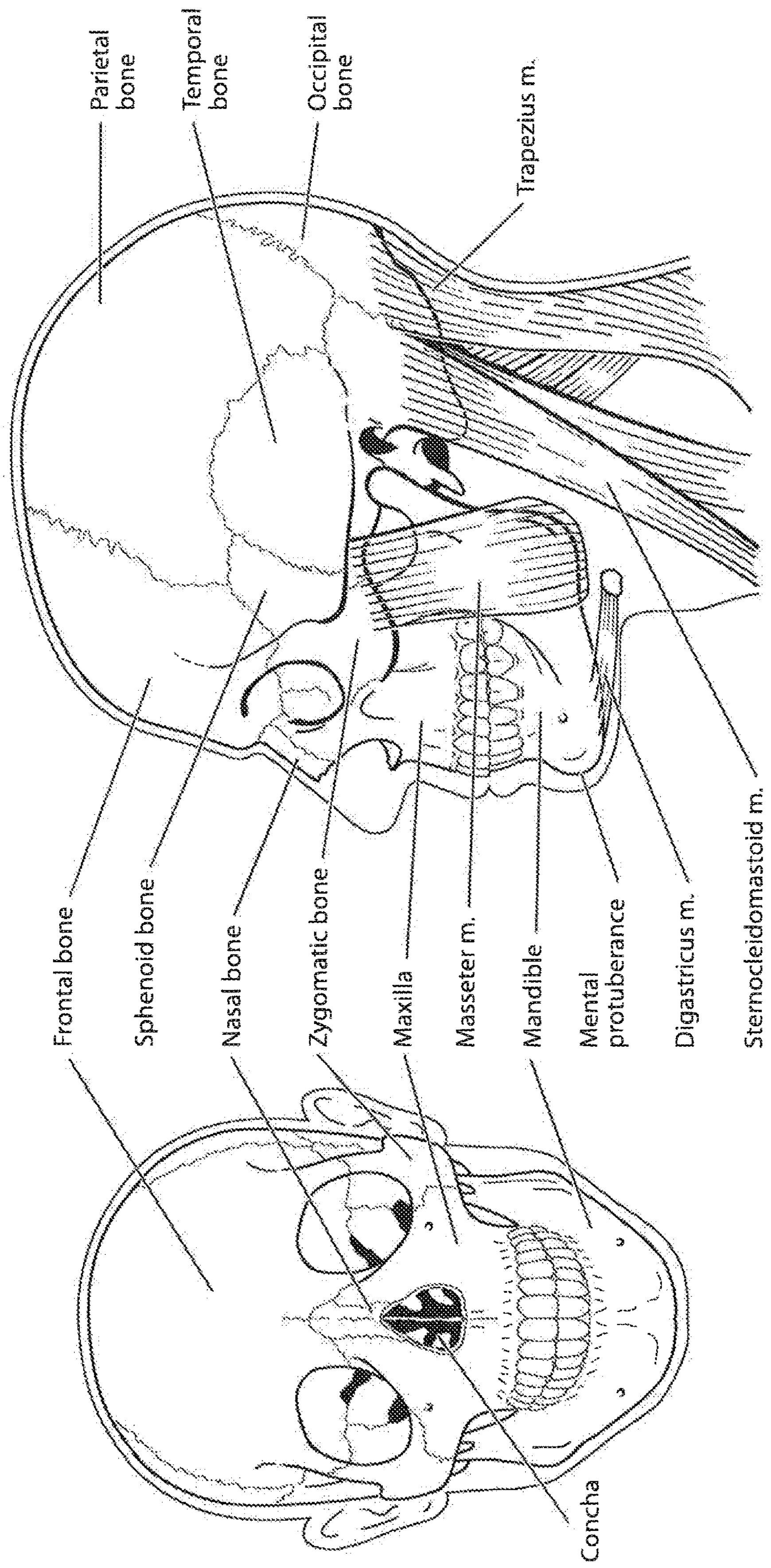

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
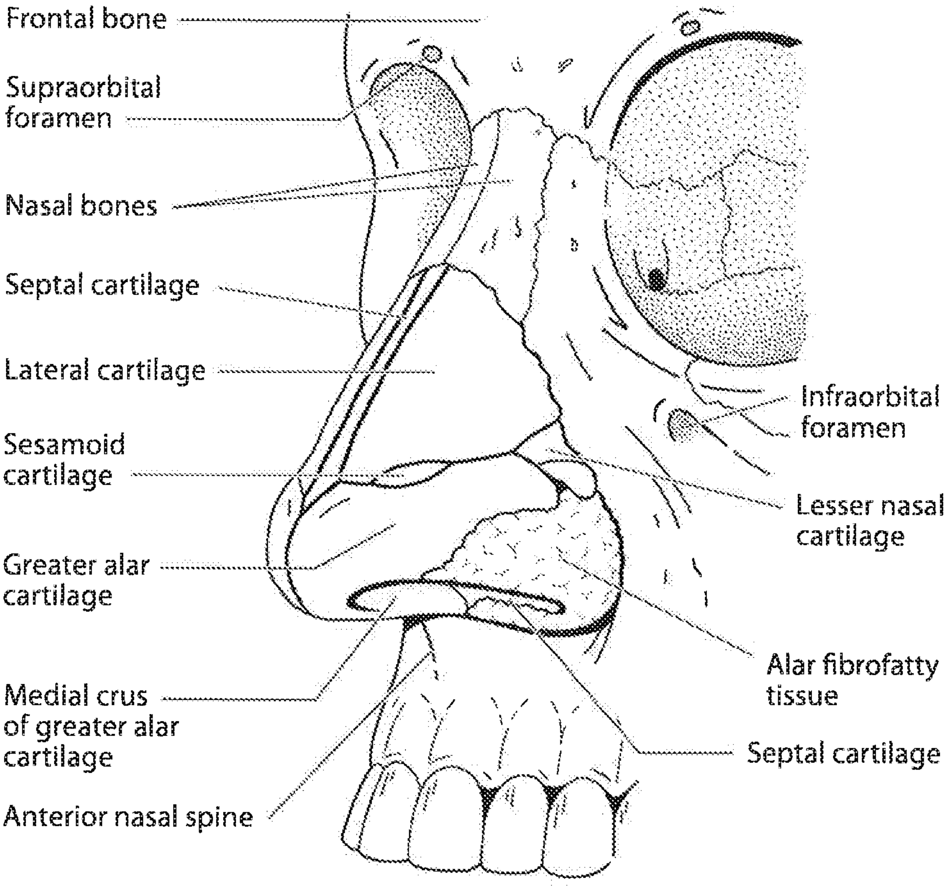

FIG. 2L shows an anterolateral view of a nose.

3.3 Patient Interface

Figure 3A:
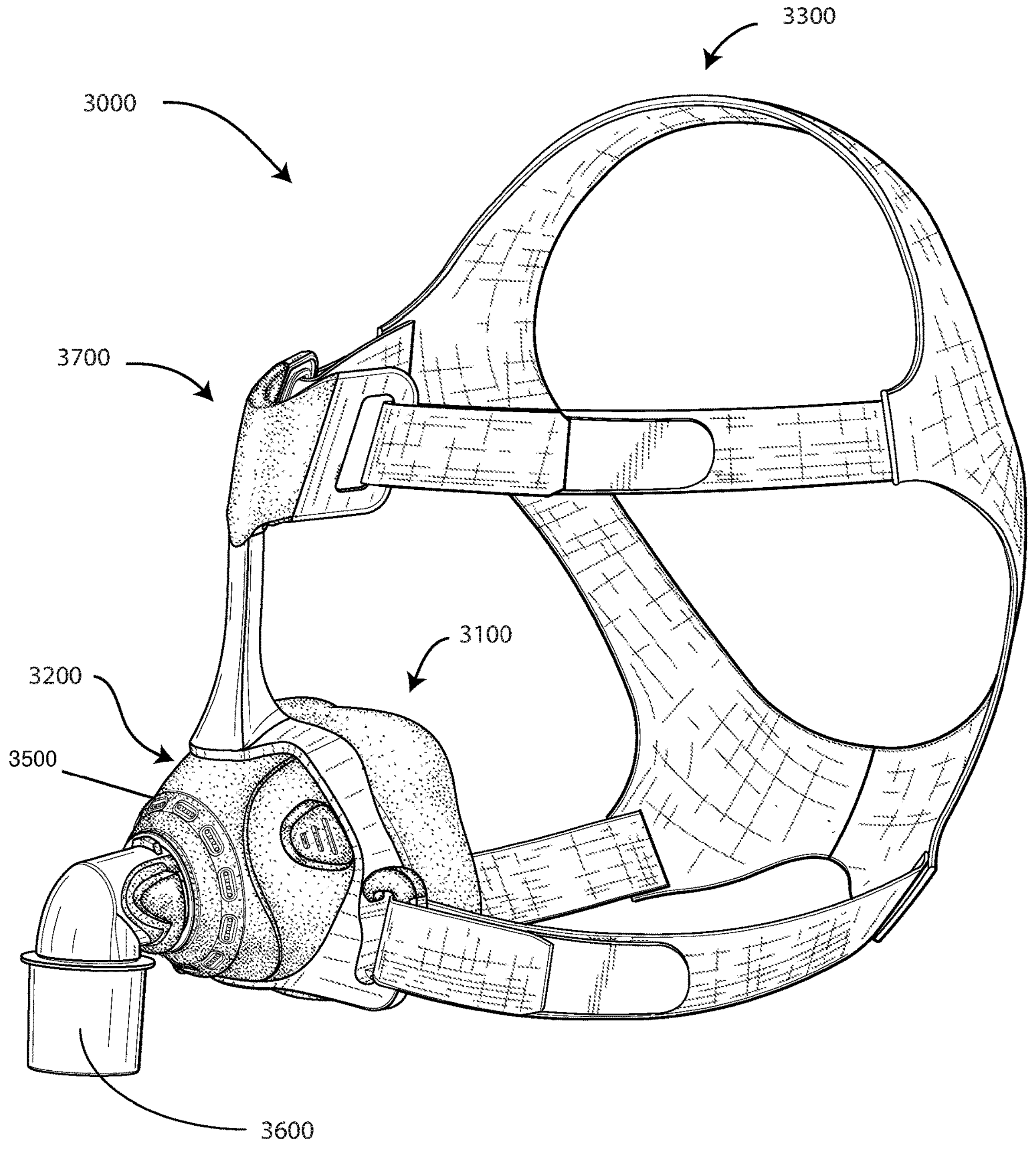

FIG. 3A shows a patient interface in the form of a nasal mask in accordance with one form of the present technology.

Figure 3B:
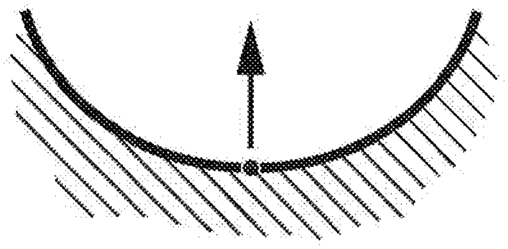

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

Figure 3C:
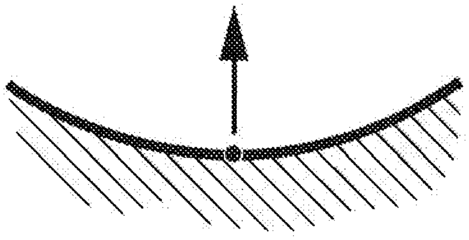

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

Figure 3D:
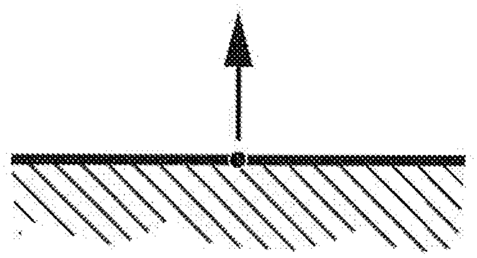

FIG. 3D shows a schematic of a cross-section through a structure at a point. An outward normal at the point is indicated. The curvature at the point has a value of zero.

Figure 3E:
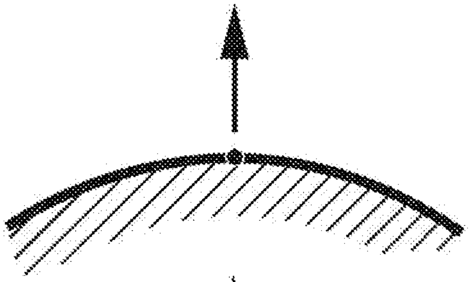

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

Figure 3F:
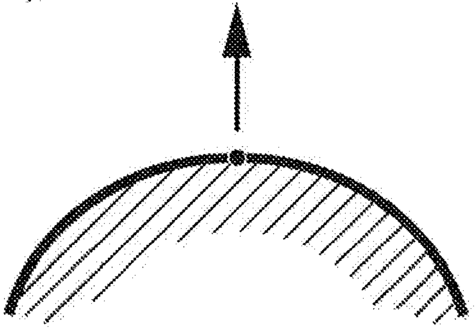

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figures 3G, 3H:
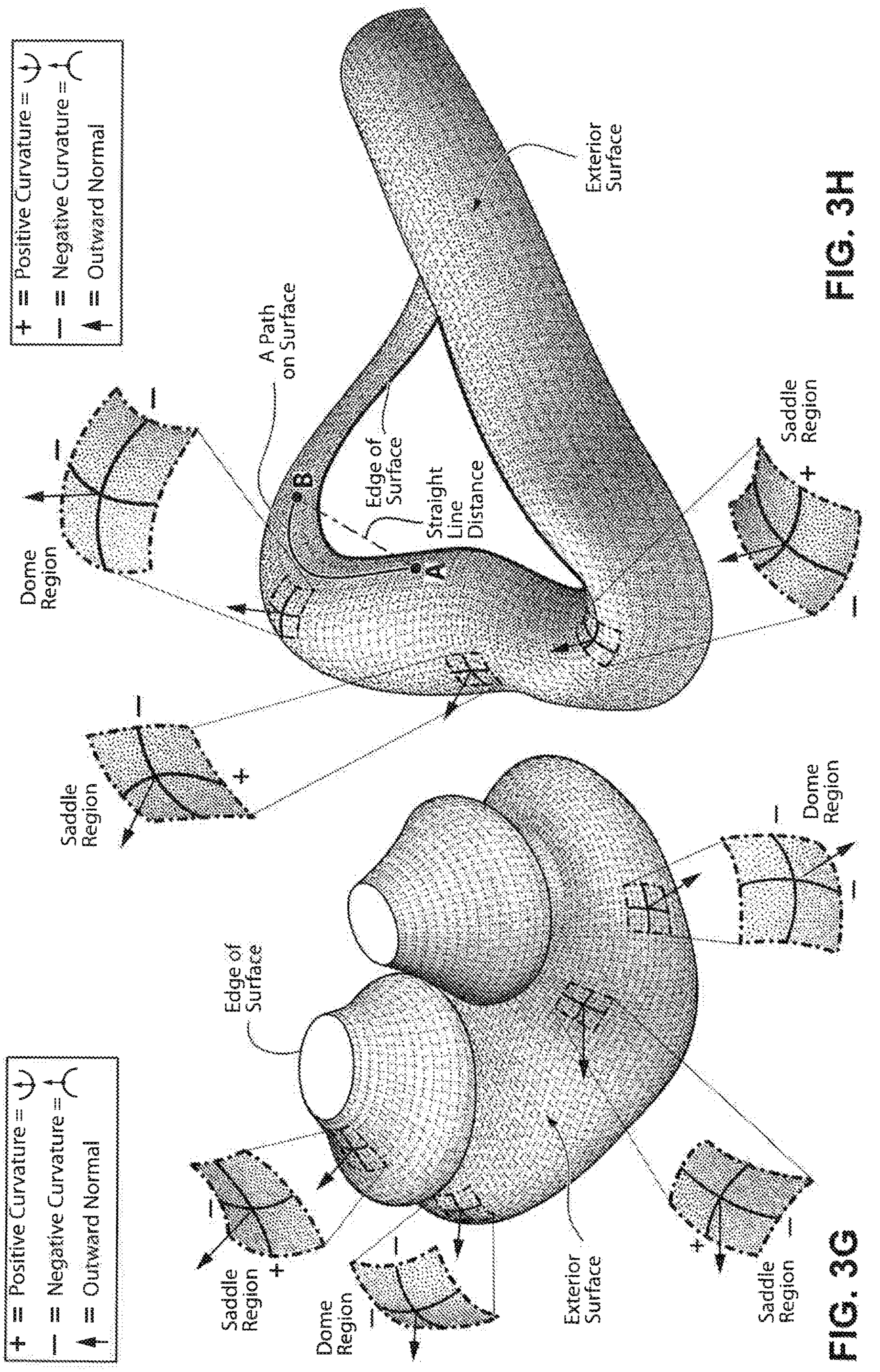

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figure 3I:
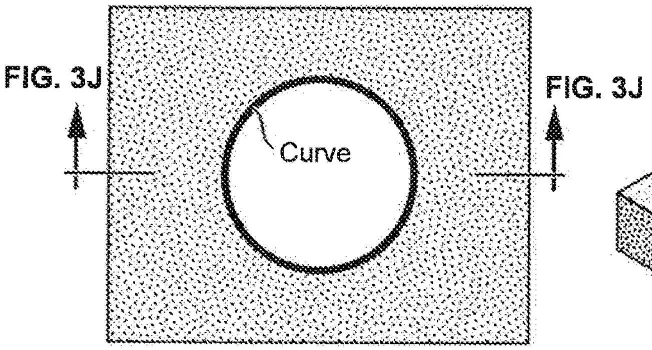

FIG. 3I shows the surface of a structure, with a one dimensional hole in the surface. The illustrated plane curve forms the boundary of a one dimensional hole.

Figure 3K:
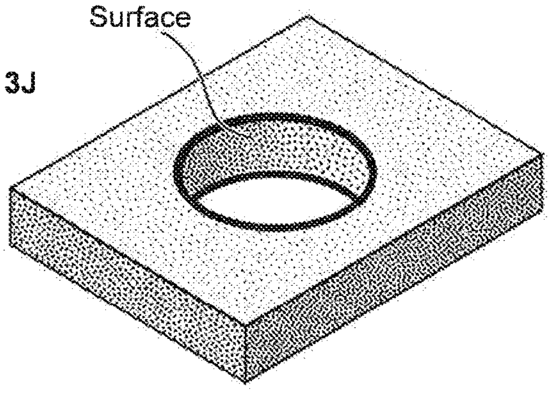
Figure 3J:
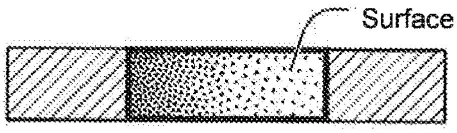

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

Figure 3L:
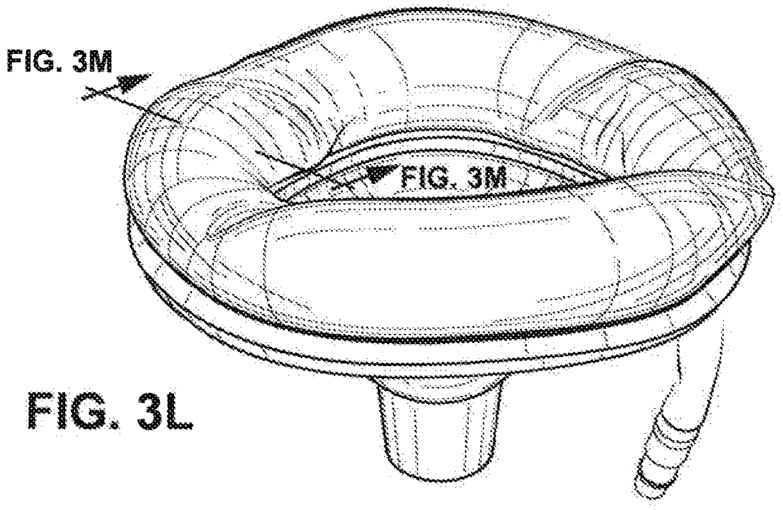

FIG. 3L shows a mask having an inflatable bladder as a cushion.

Figure 3M:
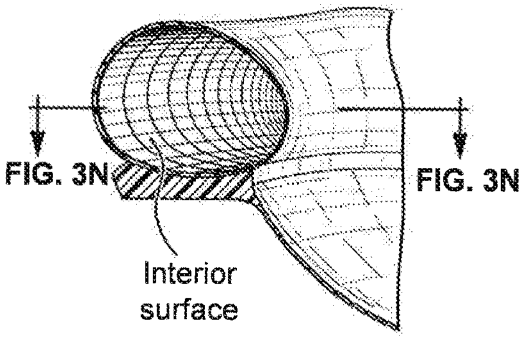

FIG. 3M shows a cross-section through the mask of FIG. 3L, and shows the interior surface of the bladder. The interior surface bounds the two dimensional hole in the mask.

Figure 3N:
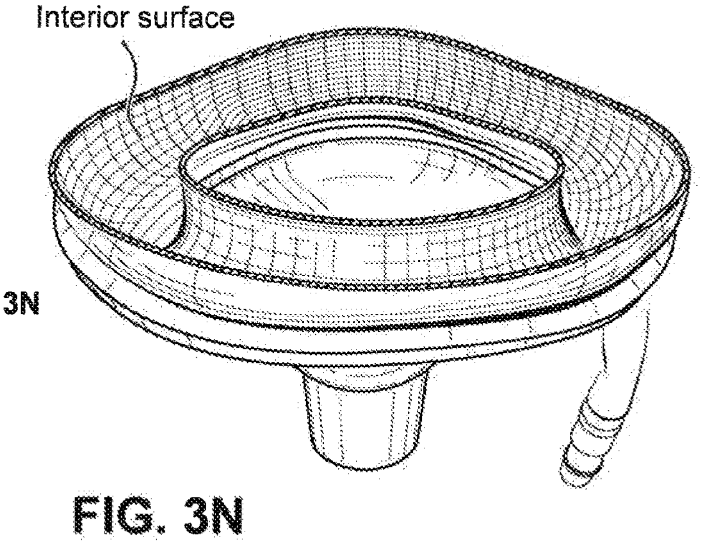

FIG. 3N shows a further cross-section through the mask of FIG. 3L. The interior surface is also indicated.

Figure 3O:
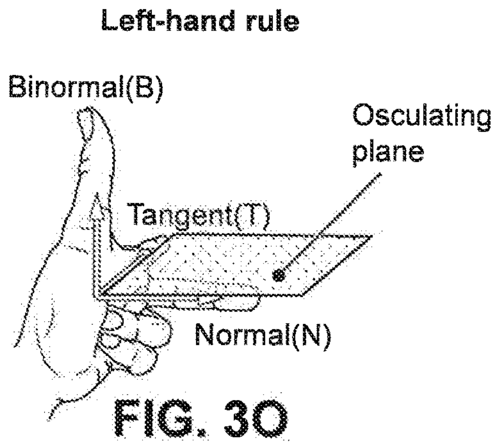

FIG. 3O illustrates a left-hand rule.

Figure 3P:
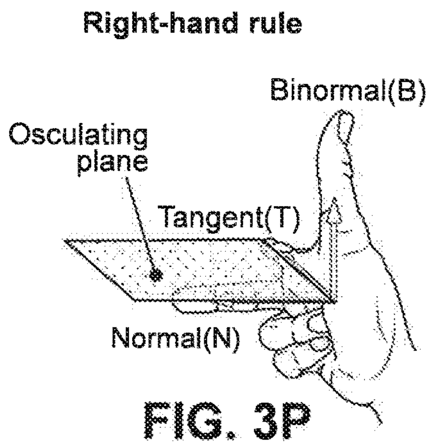

FIG. 3P illustrates a right-hand rule.

Figure 3Q:
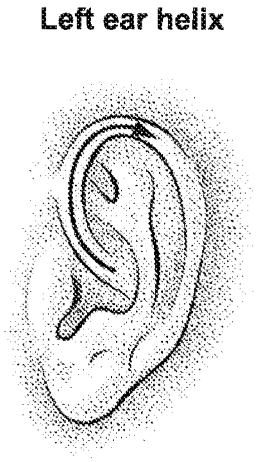

FIG. 3Q shows a left ear, including the left ear helix.

Figure 3S:
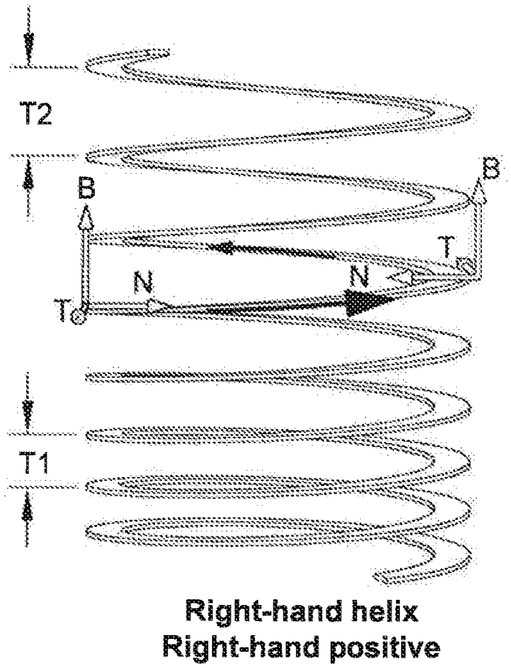
Figure 3R:
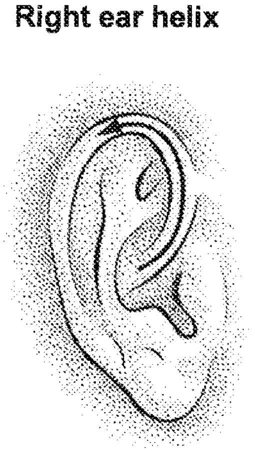

FIG. 3R shows a right ear, including the right ear helix.

FIG. 3S shows a right-hand helix.

Figure 3T:
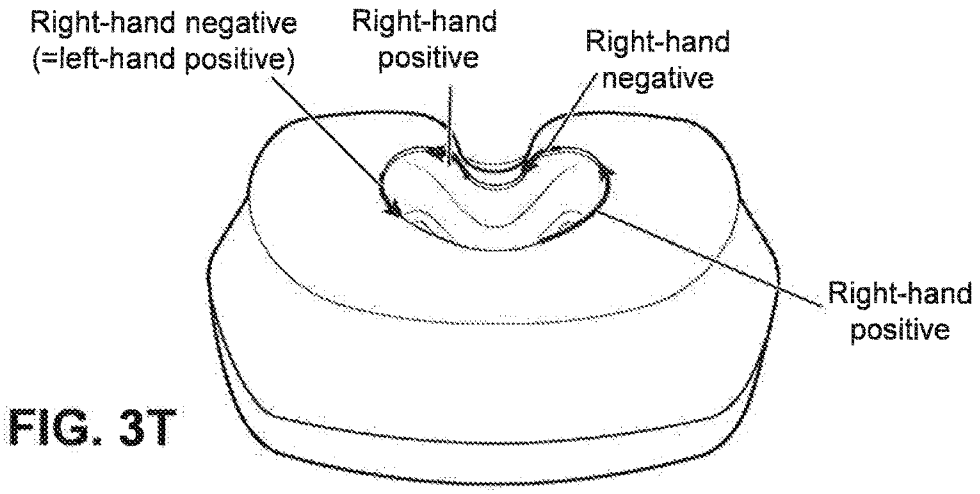

FIG. 3T shows a view of a mask, including the sign of the torsion of the space curve defined by the edge of the sealing membrane in different regions of the mask.

Figure 3U:
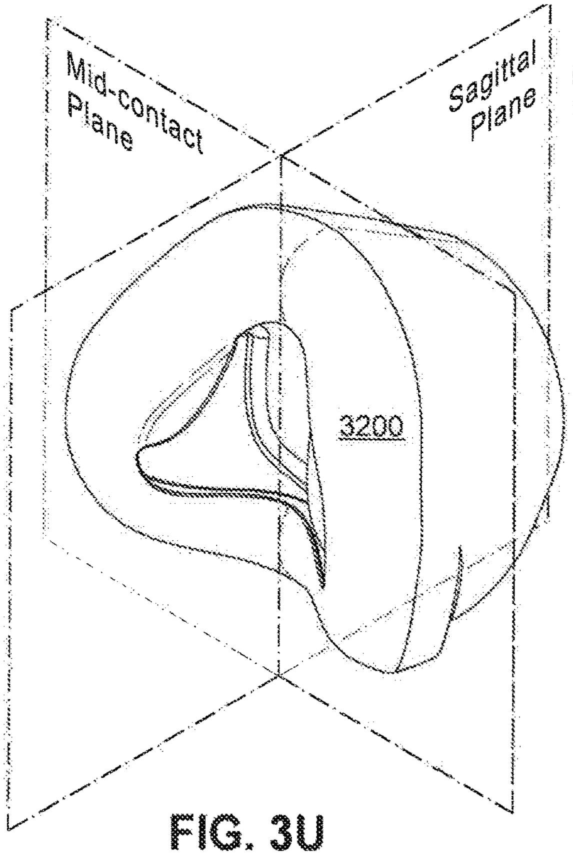

FIG. 3U shows a view of a plenum chamber 3200 showing a sagittal plane and a mid-contact plane.

Figure 3V:
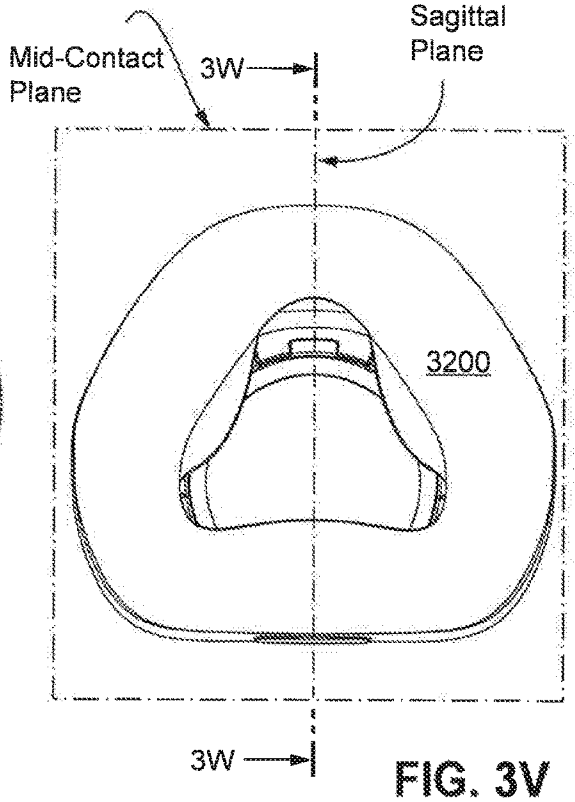

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

Figure 3W:
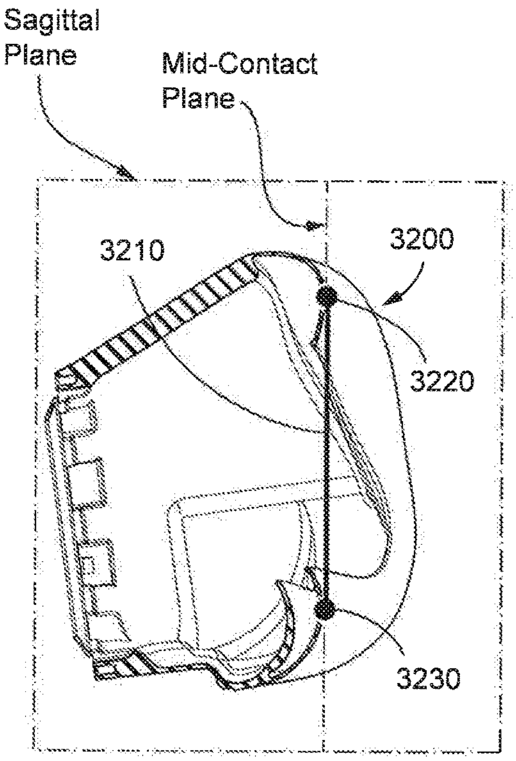

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3230. Depending on the geometry of the cushion in this region, the mid-contact plane may be a tangent at both the superior and inferior points.

Figure 3X:
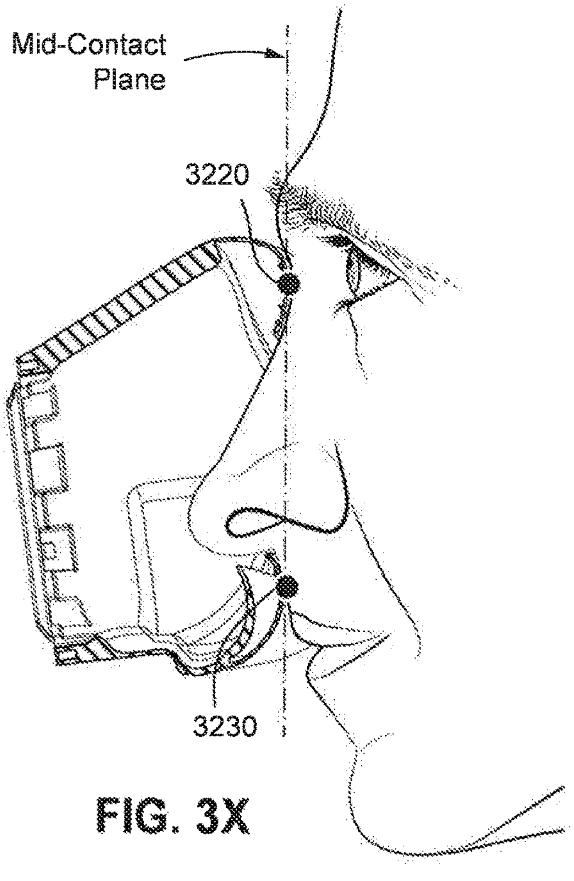

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3230 sits on the lip superior.

Figure 4:
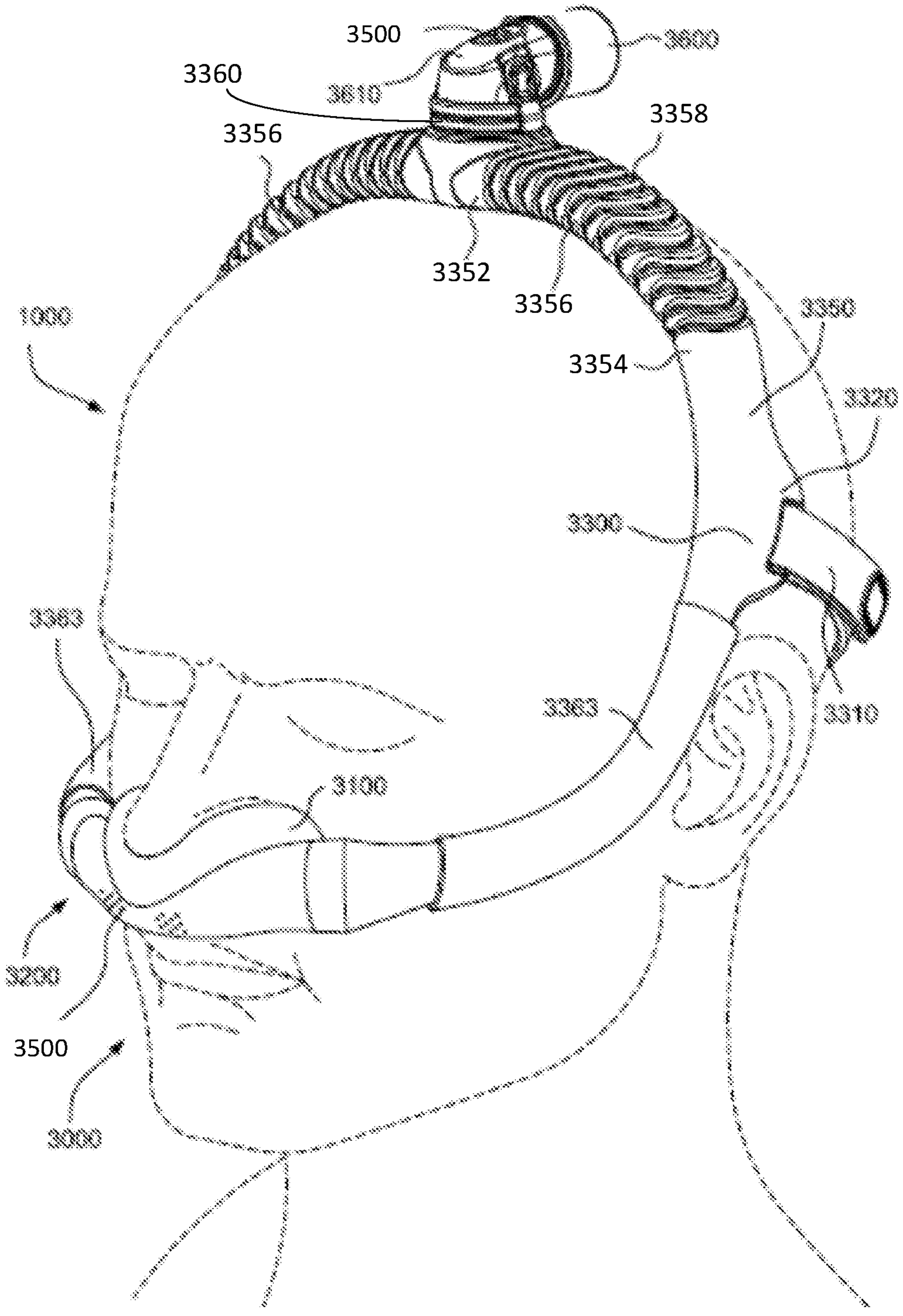

FIG. 4 shows a perspective view of a patient interface in use.

3.4 Brief Description of Drawings of the Present Technology

Figure 5:
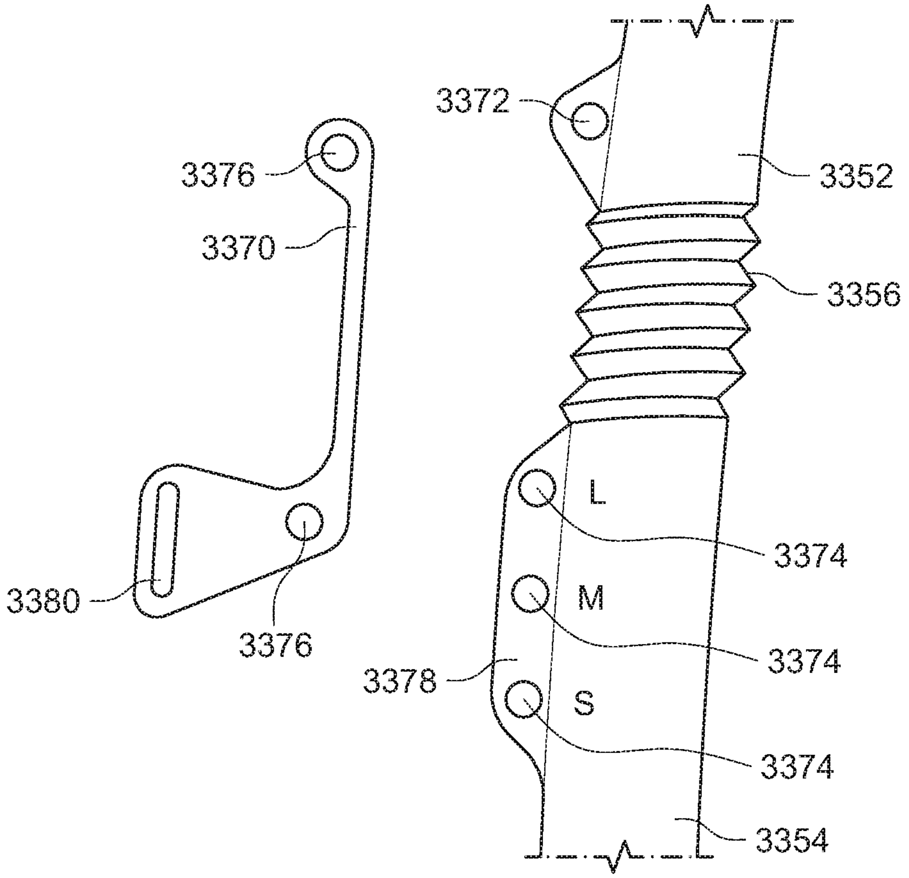

FIG. 5 shows a partial side view of a gas delivery tube and an adjustment member according to one form of the technology, with the attachment member shown detached from the gas delivery tube.

Figures 6A, 6B, 6C:
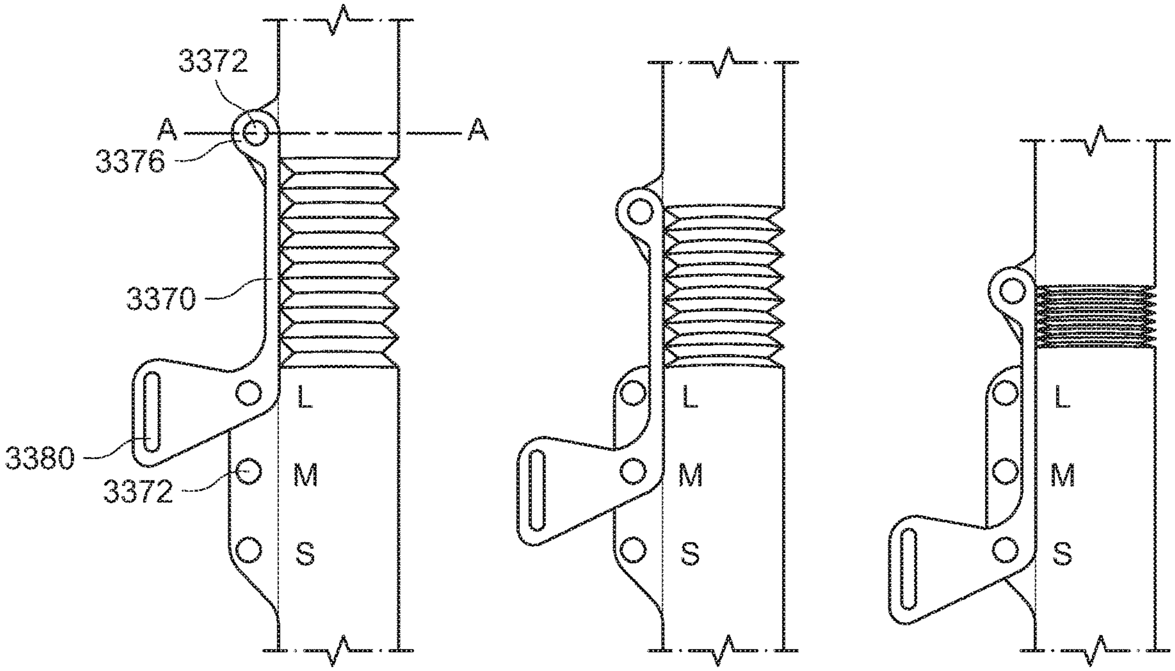

FIG. 6A. shows the gas delivery tube of FIG. 5, with the adjustment member attached to the tube in a configuration to suit large heads.

FIG. 6B. shows the gas delivery tube of FIG. 5, with the adjustment member attached to the tube in a configuration to suit medium size heads.

FIG. 6C. shows the gas delivery tube of FIG. 5, with the adjustment member attached to the tube in a configuration to suit small heads.

Figure 7:
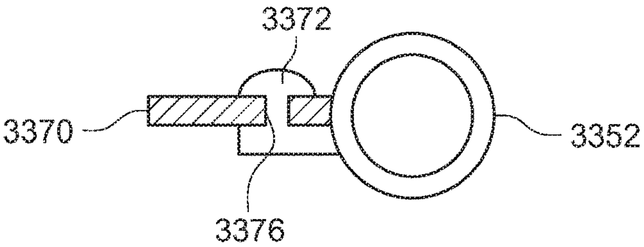

FIG. 7 shows a cross-section through plane A-A.

Figure 8:
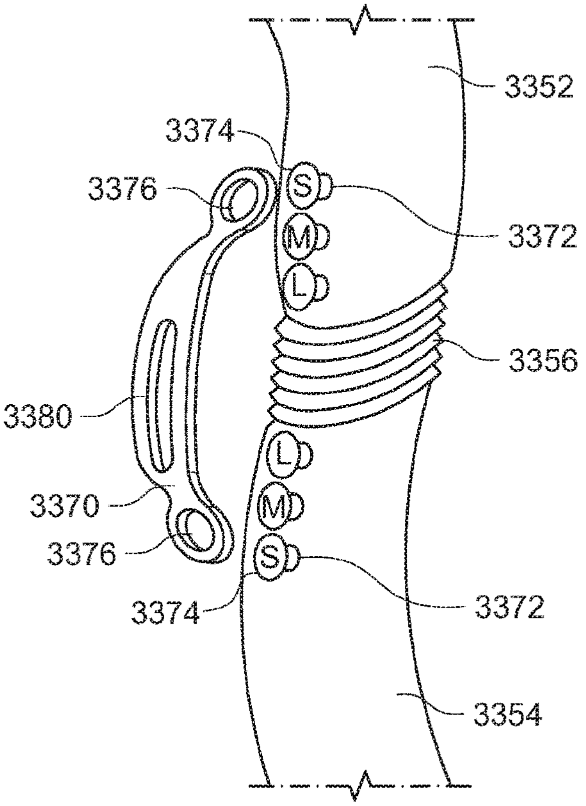

FIG. 8 shows a partial side view of a gas delivery tube and an adjustment member according to another form of the technology, with the attachment member shown detached from the gas delivery tube.

Figures 9A, 9B, 9C:
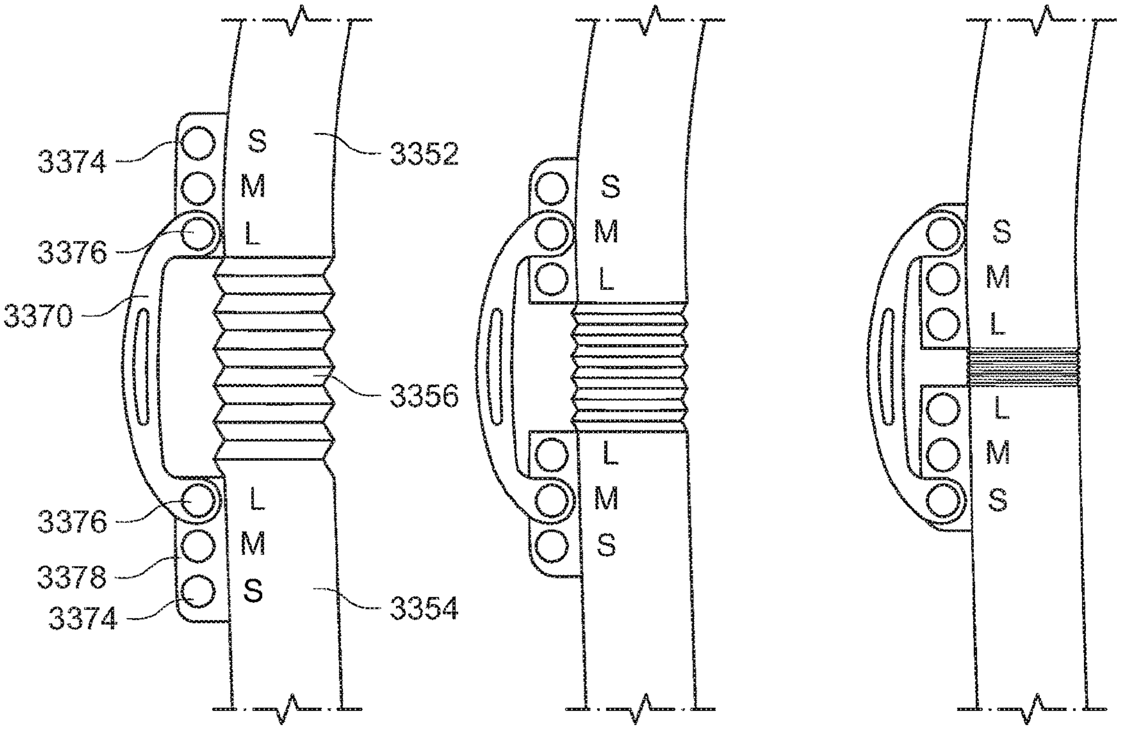

FIG. 9A. shows a partial side view of a gas delivery tube and an adjustment member according to another form of the technology, with the adjustment member attached to the tube in a configuration to suit large heads.

FIG. 9B. shows the gas delivery tube of FIG. 9A, with the adjustment member attached to the tube in a configuration to suit medium size heads.

FIG. 9C. shows the gas delivery tube of FIG. 9A, with the adjustment member attached to the tube in a configuration to suit small heads.

FIG. 10 shows a partial perspective view of a gas delivery tube and adjustment member according to another form of the technology.

FIG. 11 shows a side view of the adjustment member of FIG. 10.

FIG. 12A shows the gas delivery tube of FIG. 10 with an adjustable strap engaging portion set to a middle position.

FIG. 12B shows the gas delivery tube of FIG. 10 with an adjustable strap engaging portion set to an inferior position.

Figure 13:
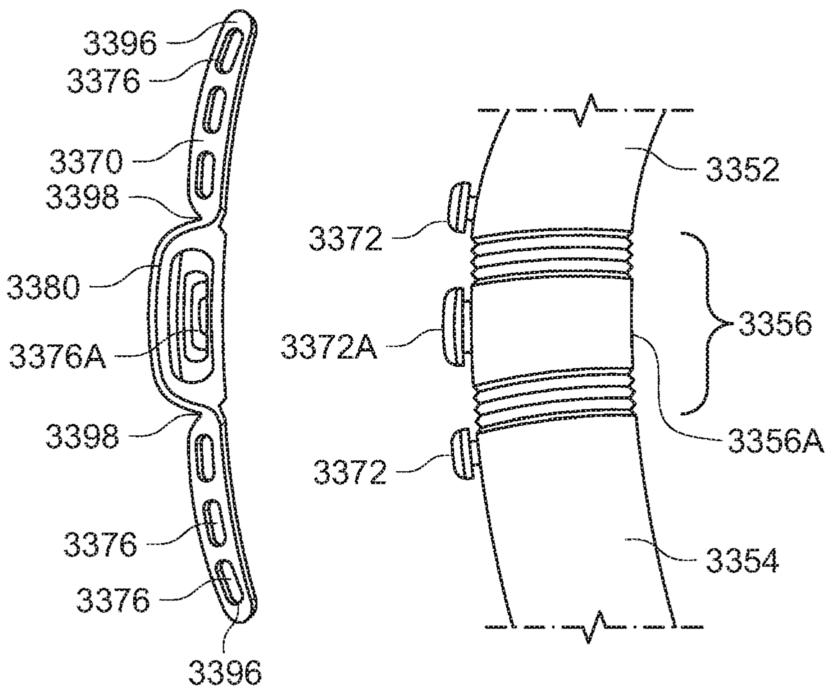

FIG. 13 shows a partial side view of a gas delivery tube and an adjustment member according to another form of the technology, with the attachment member shown detached from the gas delivery tube.

Figure 14:
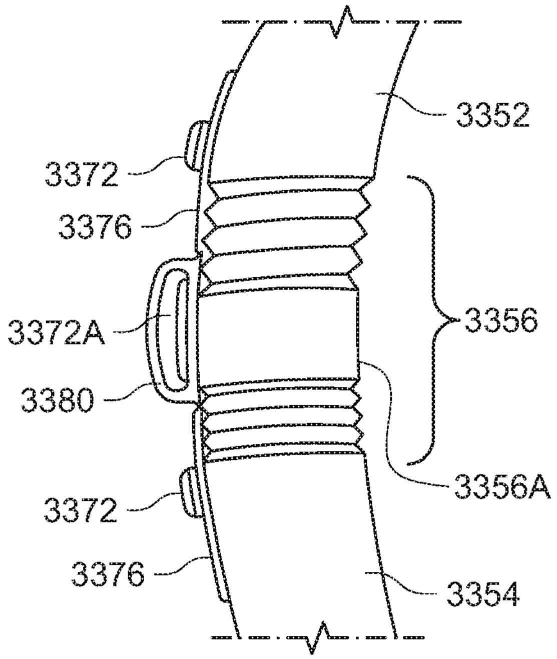

FIG. 14 shows a partial side view of the gas delivery tube and adjustment member of FIG. 13 with the attachment member connected to the gas delivery tube.

Figure 15A:
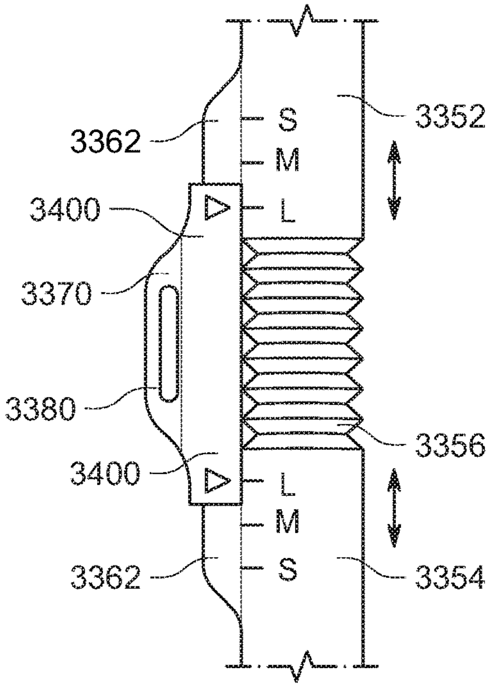

FIG. 15A shows a partial side view of a gas delivery tube and an adjustment member according to another form of the technology, with the adjustment member and tube in a configuration suitable for large heads.

Figure 15B:
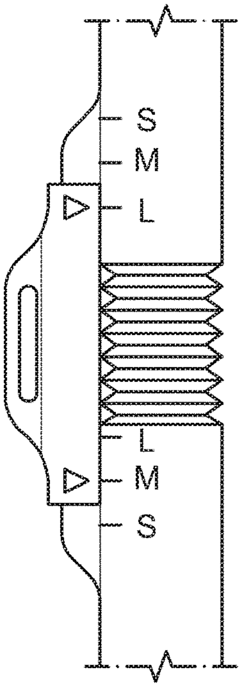

FIG. 15B shows the gas delivery tube and adjustment member of FIG. 15A with the adjustment member and tube in a configuration suitable for medium size heads.

Figure 15C:
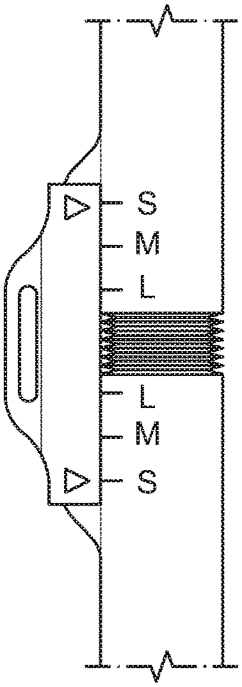

FIG. 15C shows the gas delivery tube and adjustment member of FIG. 15A with the adjustment member and tube in a configuration suitable for small heads.

Figure 16:
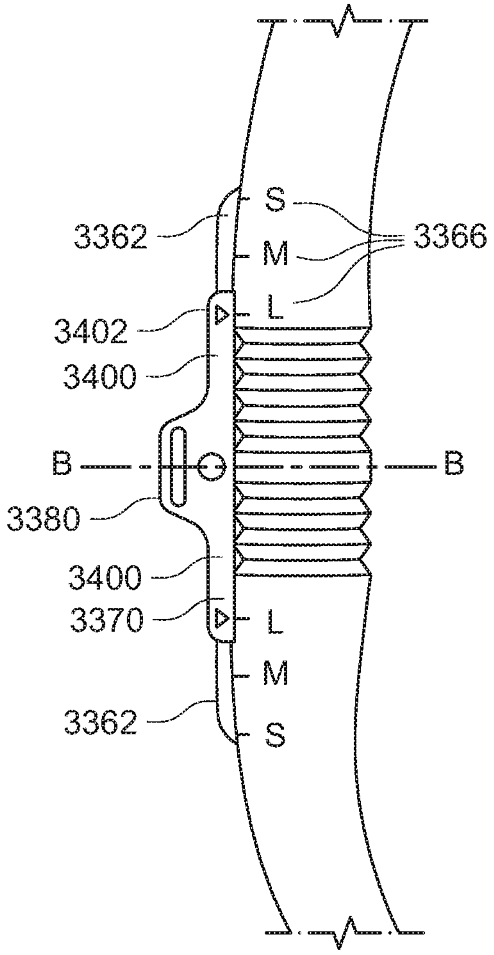

FIG. 16 shows a partial side view of a gas delivery tube and an adjustment member according to another form of the technology.

Figure 17:
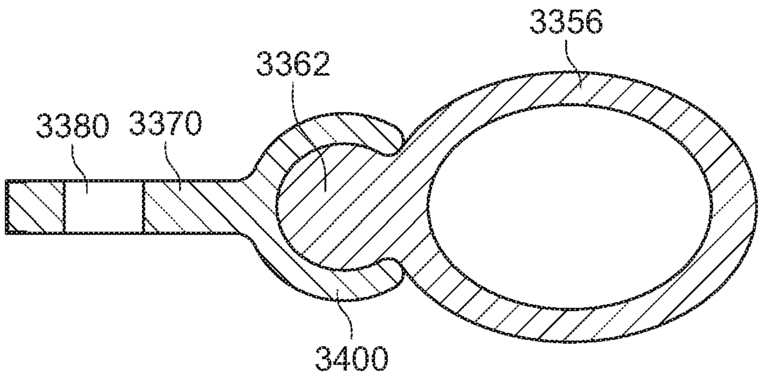

FIG. 17 shows a cross-section through plane B-B.

Figure 18:
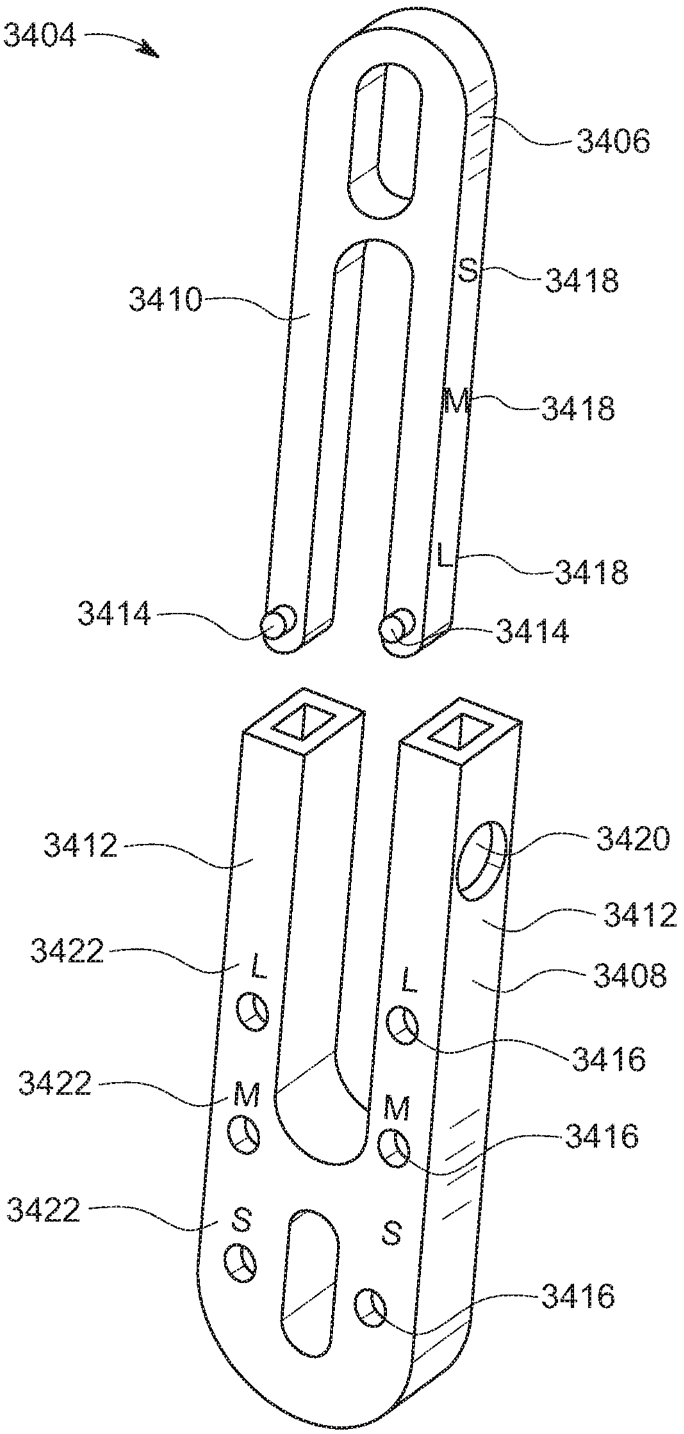

FIG. 18 shows an exploded view of a variable length adjustment means according to another form of the technology.

Figure 19:
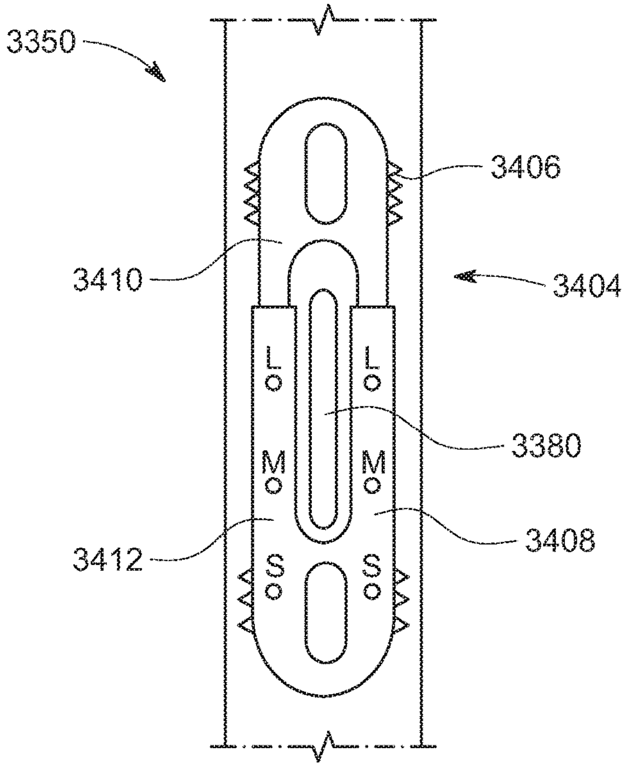

FIG. 19 shows a partial rear view of a gas delivery tube with a variable length adjustment means of FIG. 18.

Figures 20A, 20B, 20C:
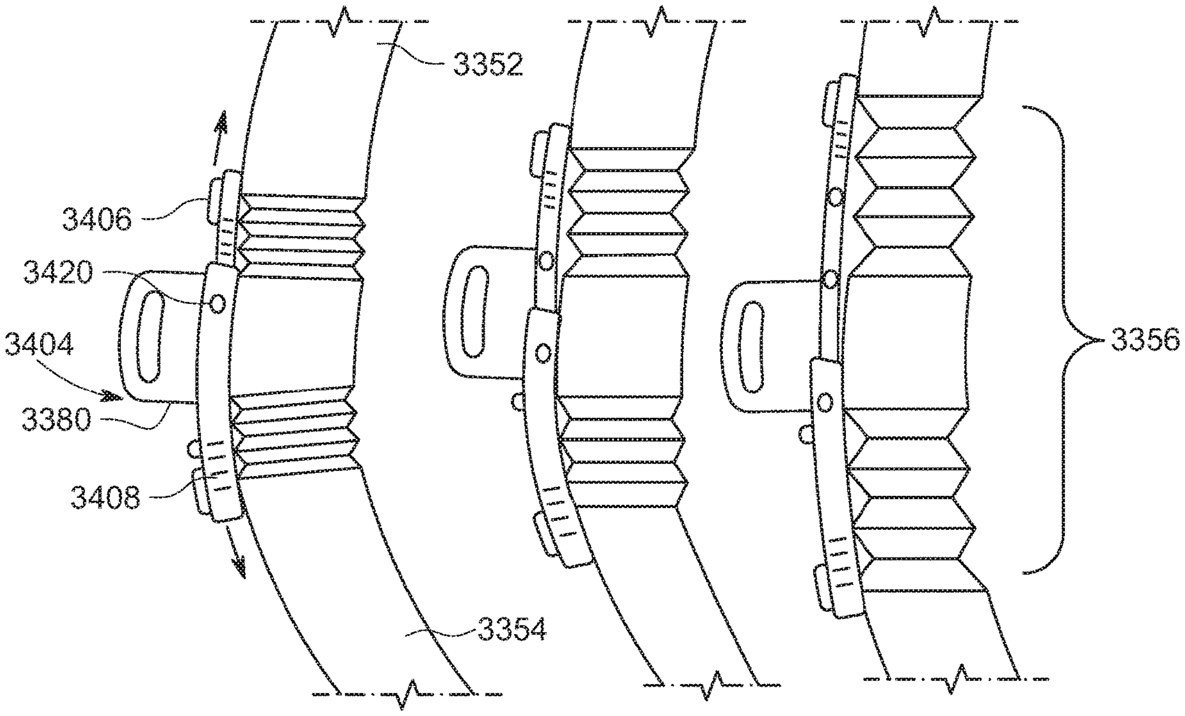

FIG. 20A shows a partial side view of a gas delivery tube with a variable length adjustment means of FIG. 18 in a configuration suitable for small heads.

FIG. 20B shows a partial side view of a gas delivery tube with a variable length adjustment means of FIG. 18 in a configuration suitable for medium size heads.

FIG. 20C shows a partial side view of a gas delivery tube with a variable length adjustment means of FIG. 18 in a configuration suitable for large heads.

Figure 21:
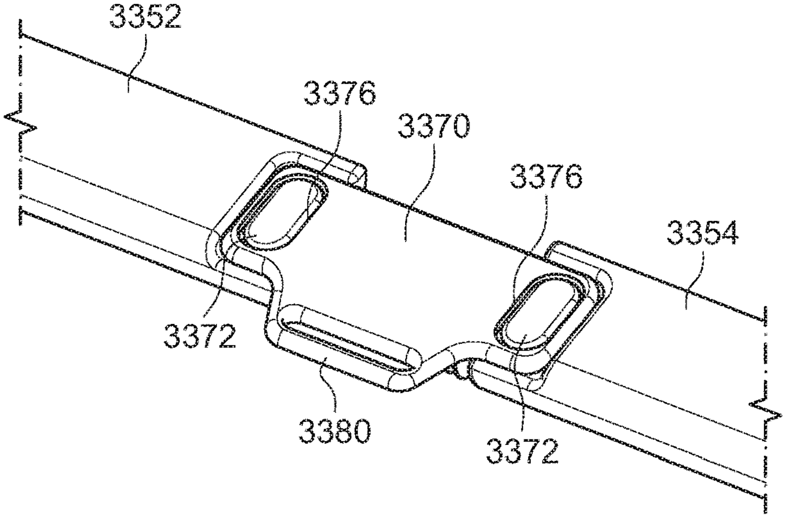

FIG. 21 shows a partial perspective view of a gas delivery tube and an adjustment member according to another form of the technology.

Figure 22:
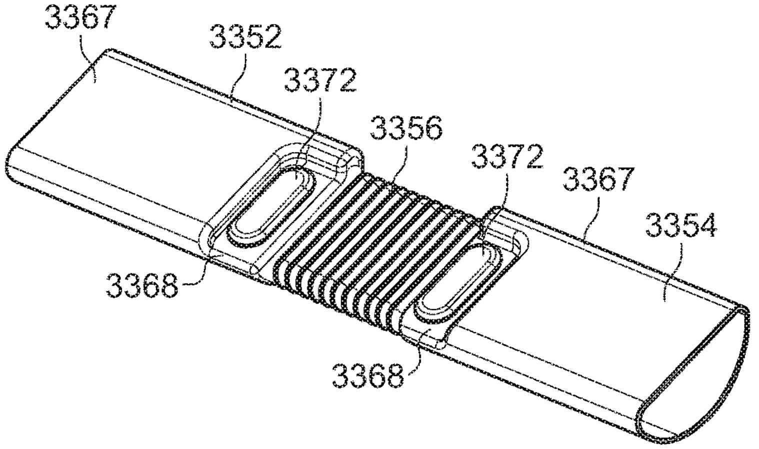

FIG. 22 shows the gas delivery tube of FIG. 21 with the adjustment member removed.

Figure 23:
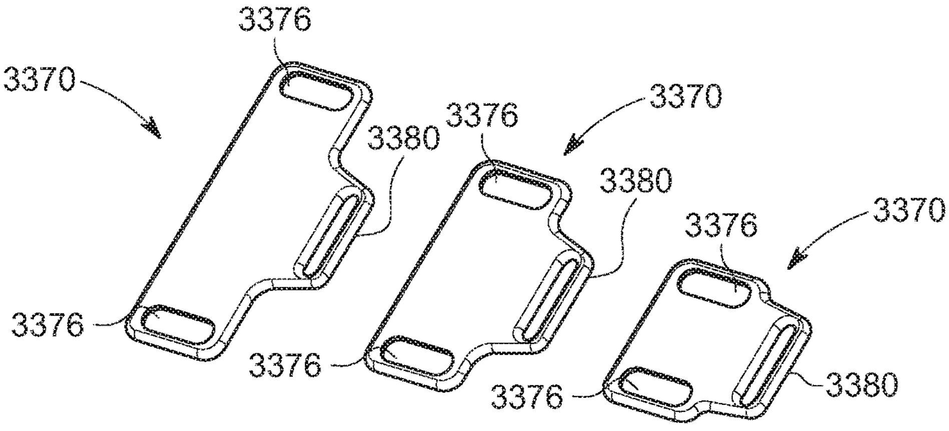

FIG. 23 shows three sizes of adjustment member suitable for use with the gas delivery tube of FIG. 21.

Figure 24:
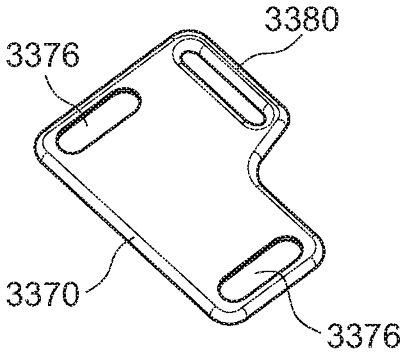

FIG. 24 shows a perspective view of an alternative form of adjustment member suitable for use with the gas delivery tube of FIG. 21.

Figure 25A:
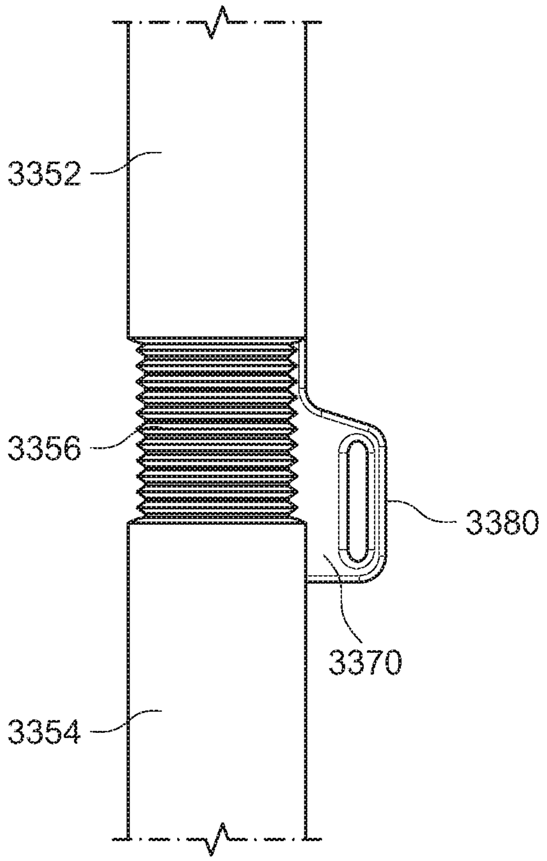

FIG. 25A shows the adjustment member of FIG. 24 engaged with a gas delivery tube in a first orientation.

Figure 25B:
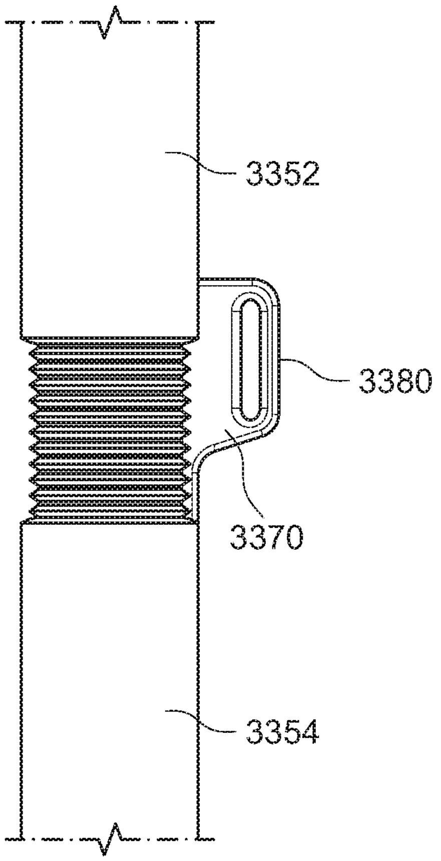

FIG. 25B shows the adjustment member of FIG. 24 engaged with a gas delivery tube in a second orientation.

Figure 26:
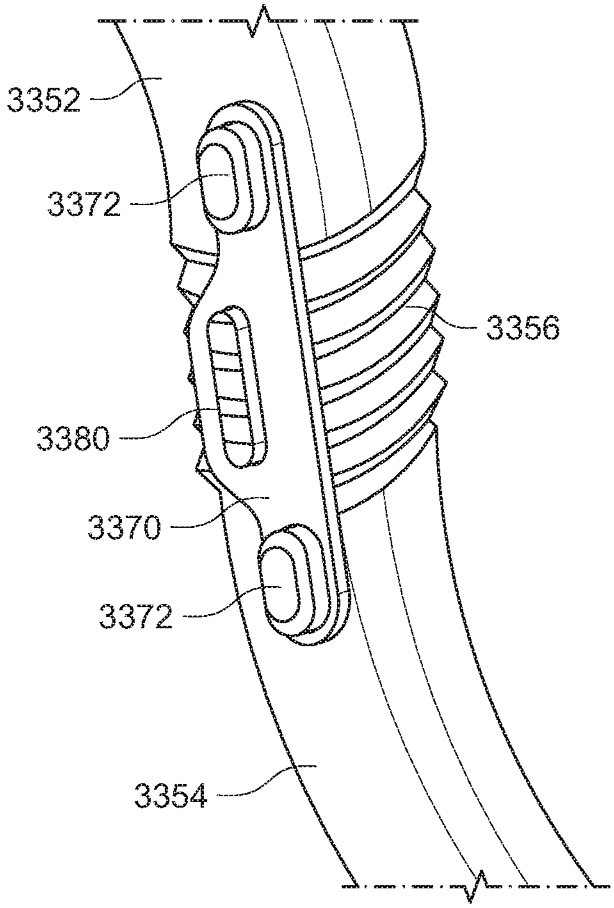

FIG. 26 shows a partial perspective view of a gas delivery tube with an adjustment member according to another form of the technology.

FIG. 27 shows a partial perspective view of a gas delivery tube and an adjustment member according to another form of the technology.

FIG. 27A shows a partial perspective view of the gas delivery tube of FIG. 27 with the adjustment member removed and a variable length portion shown in outline.

FIG. 27B shows a view from below of the adjustment member of FIG. 27.

FIG. 27C shows a transverse cross-section through the adjustment member of FIG. 27.

Figure 28:
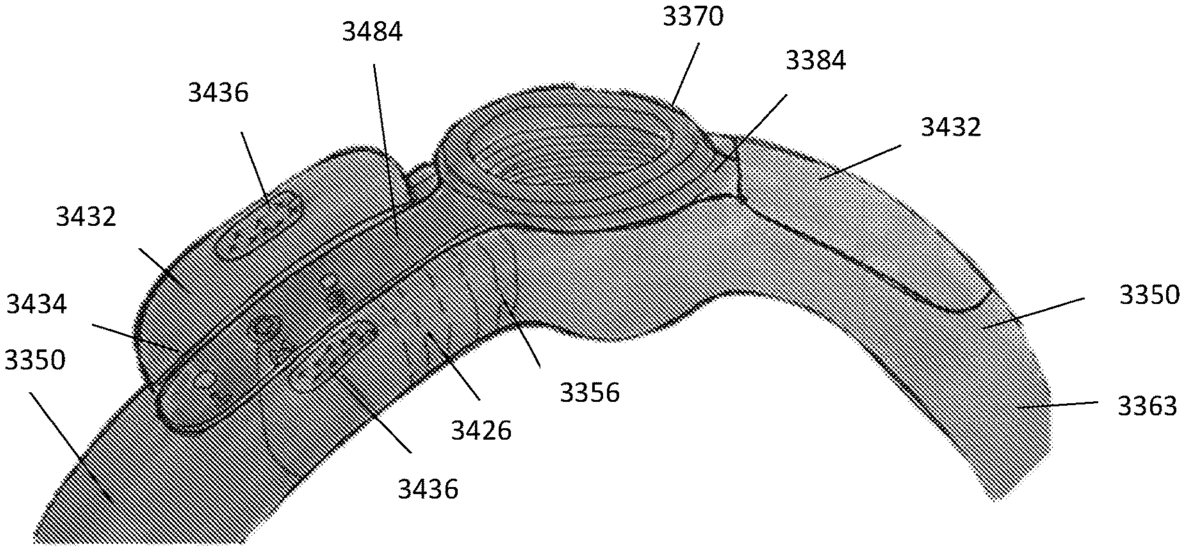

FIG. 28 shows a partial perspective view of a gas delivery tube and an adjustment member according to another form of the technology with a variable length portion shown in outline.

Figure 28A:
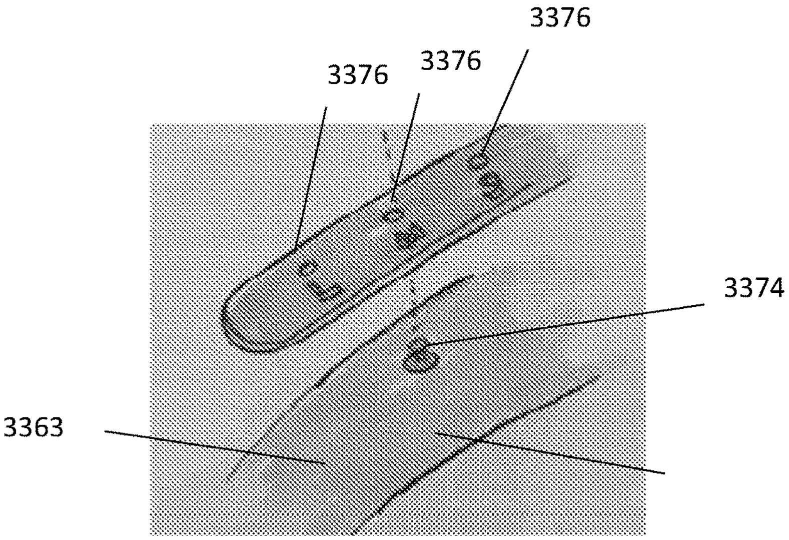

FIG. 28A is an enlarged exploded view of a portion of the adjustment member and gas delivery tube of FIG. 28.

Figure 29:
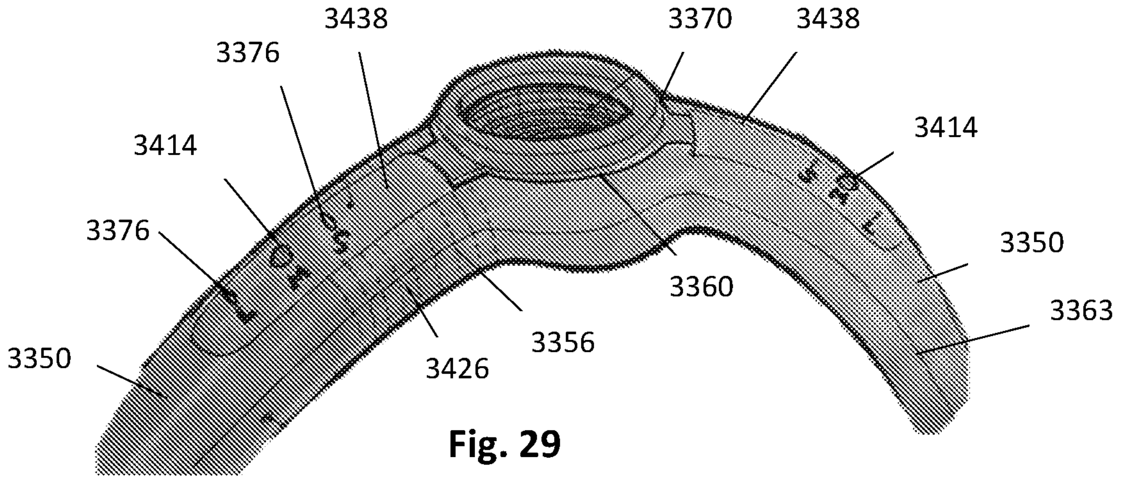

FIG. 29 shows a partial perspective view of a gas delivery tube and an adjustment member according to another form of the technology with a variable length portion shown in outline.

Figure 29A:
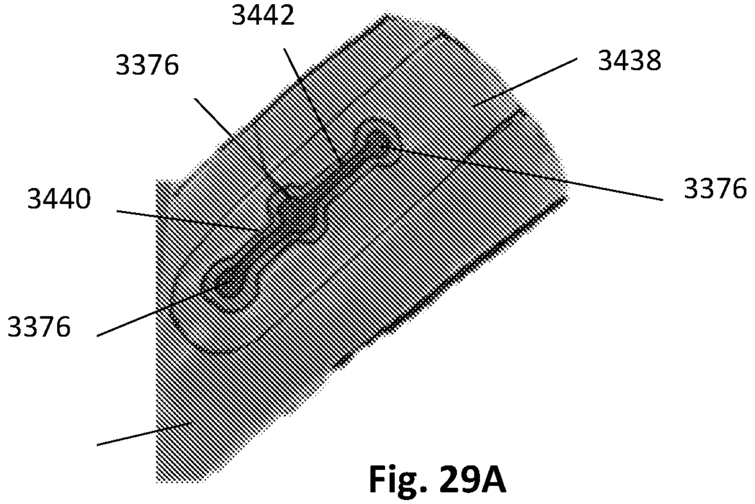

FIG. 29A shows an enlarged view of the apertures in the pocket of the sleeve of the patient interface of FIG. 29.

Figure 29B:
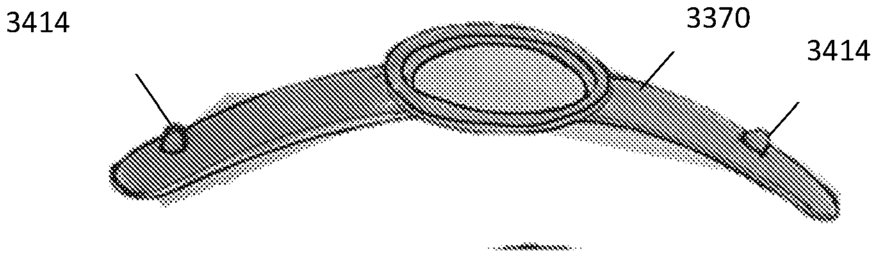

FIG. 29B shows the adjustment member of FIG. 29.

Figure 30:
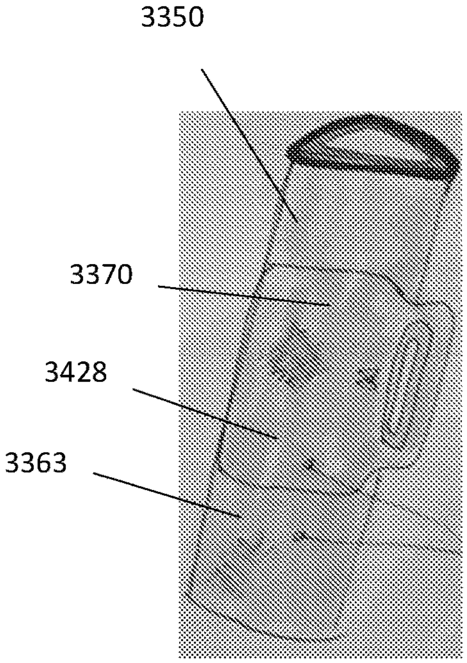

FIG. 30 shows a partial side view of a gas delivery tube and an adjustment member according to another form of the technology.

Figure 30A:
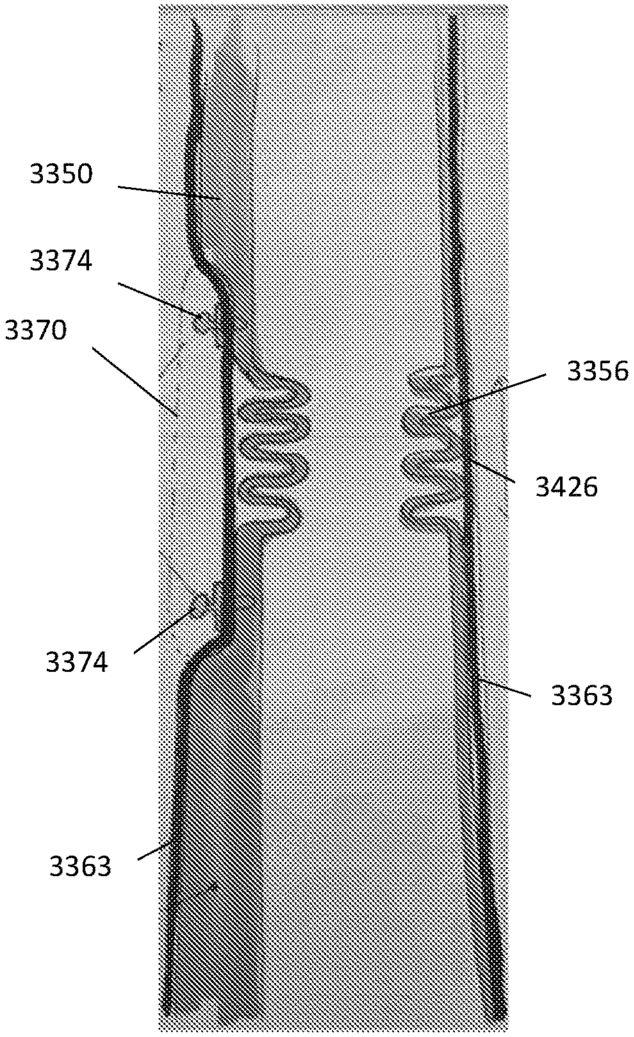

FIG. 30A shows a cross-section through the gas delivery tube of FIG. 30, with the adjustment member shown in outline.

Figure 30B:
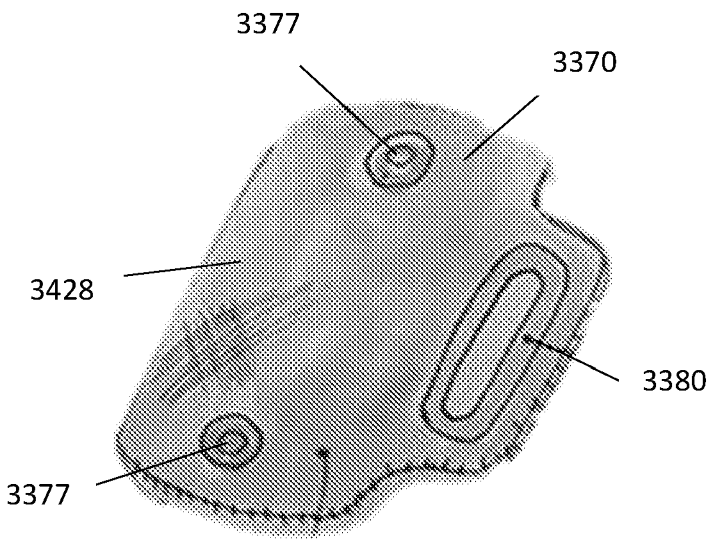

FIG. 30B shows a perspective view of the adjustment member of FIG. 30.

Figure 30C:
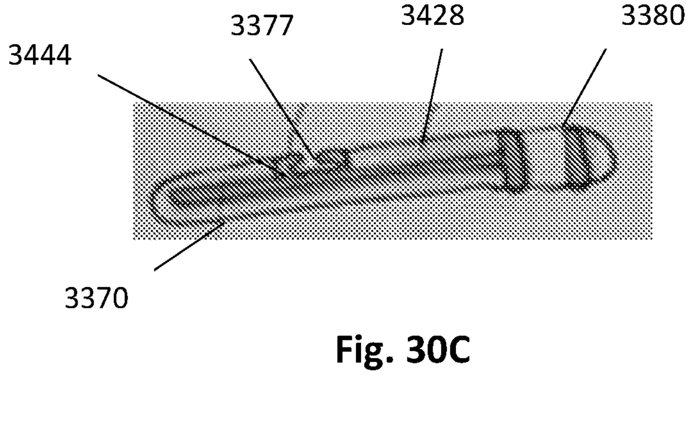

FIG. 30C is a cross-section view of the adjustment member of FIG. 30B.

4 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

4.1 Therapy

In one form, the present technology comprises a method for treating a respiratory disorder comprising applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

4.2 Respiratory Therapy Systems

In one form, the present technology comprises a respiratory therapy system for treating a respiratory disorder. The respiratory therapy system may comprise an RPT device 4000 for supplying a flow of air to the patient 1000 via an air circuit 4170 and a patient interface 3000.

4.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3500, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to maintain positive pressure at the entrance(s) to the airways of the patient 1000. The sealed patient interface 3000 is therefore suitable for delivery of positive pressure therapy.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 $cmH_2O$ with respect to ambient.

The patient interface 3000 in accordance with one form of the present technology is constructed and arranged to be able to provide a supply of air at a positive pressure of at least 10 $cmH_2O$ with respect to ambient.

The patient interface 3000 in accordance with one form of the present technology is constructed and arranged to be able to provide a supply of air at a positive pressure of at least 20 $cmH_2O$ with respect to ambient.

4.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

4.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

4.3.1.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

4.3.1.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

4.3.1.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

4.3.1.5 Forehead Region

In one form, the seal-forming structure that forms a seal in use on a forehead region of the patient's face. In such a form, the plenum chamber may cover the eyes in use.

4.3.1.6 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

4.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

4.3.3 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap, In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another. suitable for a small sized head, but not a large sized head.

In some forms of the present technology, the positioning and stabilising structure 3300 comprises one or more gas delivery tubes 3350 that deliver pressurised air received from a conduit forming part of the air circuit 4170 from the RPT device to the patient's airways, for example as shown in FIG. 4.

In examples, the positioning and stabilising structure 3300 comprises two tubes 3350 that deliver air to the seal-forming structure 3100 from the air circuit 4170. The tubes 3350 are an integral part of the positioning and stabilising structure 3300 of patient interface 3000 to position and stabilise the seal-forming structure 3100 of the patient interface to the appropriate part of the patient's face (for example, the nose or the nose and mouth). This allows the conduit of air circuit 4170 providing the flow of pressurised air to connect to a connection port 3600 of the patient interface in a position other than in front of the patient's face, which may be unsightly to some people. While the use of a pair of tubes 3350 has some advantages, in some examples the positioning and stabilising structure 3300 comprises only a single tube 3350 configured to overlie the patient's head on one side. A strap or other stabilising component may be provided to the other side of the patient's head between the top end of the single tube 3350 and the seal-forming structure 3100, to provide balanced forces on the seal-forming structure 3100. Except where specifically stated otherwise, any of the examples of positioning and stabilising structures described below with reference to FIGS. 5-30 may comprise a single tube 3350 or two tubes 3350.

In certain forms of the present technology, at least one of the gas delivery tubes 3350 is constructed and arranged to contact, in use, at least a region of the patient's head superior to an otobasion superior of the patient's head.

The patient interface 3000 may comprise a connection port 3600 located proximal a top, side or rear portion of a patient's head. For example, in the form of the present technology illustrated in FIG. 4, the connection port 3600 is located on top of the patient's head, e.g. overlying the parietal bone. In this example the patient interface 3000 comprises an elbow 3610 to which the connection port 3600 is provided. The elbow 3610 may swivel with respect to the positioning and stabilising structure 3300 in order to decouple movement of a conduit connected to the connection port 3600 from the positioning and stabilising structure 3300. The elbow 3610 may connect to a fluid connection opening 3360 in the headgear tubing 3350 or in a component to which the headgear tubing 3350 is connected. Additionally, or alternatively, a conduit connected to the connection port 3600 may swivel with respect to the elbow 3610. In the illustrated example, elbow 3610 comprises a swivelling conduit connector comprising the connection port 3600 to which a conduit of the air circuit 4170 is able to connect, such that the conduit can rotate about its longitudinal axis with respect to the elbow 3610. In some examples the air circuit 4170 may connect to the fluid connection opening 3360. The elbow 3610 may rotatably connect to the fluid connection opening 3360 or to a ring received in the fluid connection opening 3360.

In the example shown in FIG. 4, the two tubes 3350 are integrally formed and comprise a fluid connection opening 3360 to which the swivel elbow connects. In other examples, where separate tubes are used, they may be indirectly connected together, for example each may be connected to a T-shaped conduit having two conduit arms each fluidly connectable to the tubes 3350. The crown connector may comprise a third conduit arm. The connection port 3600 may comprise an elbow 3610 received at the centre of the crown connector 3360. The elbow 3610 may be configured to swivel.

In certain examples of the present technology, the tubes 3350 are configured to receive a strap 3310 (for example by provision of tabs 3320) at the locations superior to and proximate the patient's ears.

In some forms of the technology a textile sleeve 3363 may be provided over a portion of each tube 3350.

At least one of the gas delivery tubes 3350 comprises a first (e.g. superior) portion 3352, a second (e.g. inferior) portion 3354 and a variable length portion 3356 which extends between the first and second portions 3352, 3354. The variable length portion 3356 may be extendable, compressible, or both extendable and compressible from its "at rest" or natural length. In examples, the variable length portion 3356 comprises at least one corrugated or concertina portion 3358. Varying the length of the variable length portion 3356 has the effect of varying the total length of the gas delivery tube 3350. In many examples the length of the first portion 3352 is greater than that shown in FIG. 4, e.g. such that the inferior end of the variable length portion 3356 is only slightly superior to the patient's ear.

In embodiments the length of the variable length portion 3356 (and therefore the length of the gas delivery tube 3350) can be adjusted (e.g. set to a required length) by use of an adjustment member 3370, as described further below.

In one form of the technology the adjustment member 3370 is substantially inextensible. In examples the adjustment member 3370 may be substantially rigid, but in other examples a substantially flexible adjustment member 3370 may be used.

4.3.3.1 Tube with Multiple Connectors

Referring next to FIGS. 5 to 9, in one example the adjustment member 3370 is attachable (or permanently attached) to one of the first and second tube portions 3352, 3354 (e.g. the first portion 3352) and is releasably connectable to the other portion (e.g. the second portion 3354) at one of a plurality of locations. In the example shown in FIGS. 5-7, the second portion 3354 is provided with a plurality of attachment means 3372 in the form of "mushroom" shaped connector portions or formations 3374. The adjustment member 3370 comprises an aperture 3376 which is configured to be engageable with a selected one of the connectors 3374. The aperture 3376 may be provided at one end of the adjustment member 3370, or may be spaced apart from the end of the adjustment member 3370.

The connectors 3374 are spaced apart in the longitudinal or length direction of at least the second portion 3354 of the tube, and so connecting the adjustment member 3370 to a particular one of the connectors 3374 sets the length of the variable length portion 3356 of tube (and therefore the total length of the tube 3350). Those skilled in the art will appreciate that in use, the gas delivery tube 3350 will be held in tension, and so even if the adjustment member 3370 is flexible and/or axially compressible, it too will be held in tension in use.

In the example shown in FIGS. 5-7, the posterior sides of the second tube portions are provided with a rib 3378 from which the attachment means 3372 extend. The rib may extend longitudinally along the posterior of the tube. The attachment means 3372 extend laterally from the rib 3378. In other examples (for example, as shown in FIG. 14) the connectors 3374 may extend directly from the surface of the tube 3350. In the example shown in FIG. 8 the connectors 3374 extend in a posterior direction from a posterior surface of the tube 3350.

The connectors 3374 are spaced such that the overall length of the gas delivery tube 3350 can be varied to suit patients with different sized heads by changing which of the connectors 3374 the aperture 3376 of the adjustment member 3370 is engaged with. In one example the range of adjustment possible may mean that a single example of a positioning and stabilising structure 3300 can be used with the majority of patient head sizes (for example 90% of the adult population). In another example a smaller range of adjustment may be provided, for example such that the positioning and stabilising structure can be adjusted to suit 75% of the adult population or 50% of the adult population.

In examples of the technology, the variable length portion 3356 is under substantially no load (e.g. is neither compressed or extended) when the positioning and stabilising structure is adjusted to the middle of its possible range of adjustments.

In examples, the adjustment member 3370 is provided with a strap engaging portion 3380, e.g. a loop, eye or slot, for engaging a strap 3310, e.g. a back strap. In one form of the technology the strap engaging portion 3380 is provided at one end of the adjustment member 3370, e.g. adjacent the aperture 3376 (as shown in FIGS. 5 and 6). In other examples the strap engaging portion 3380 is provided between the ends of the adjustment member 3370, for example toward or at the middle of the length of the adjustment member 3370 (as shown in FIGS. 8 and 9).

Any number of connectors may be provided (for example 1, 2 or 3), but in the example shown in FIGS. 5 and 6, three connectors 3374 are provided to the second portion 3354 of the tube, such that the headgear can be adjusted to suit patients with large heads (FIG. 6A), medium heads (FIG. 6B) or small heads (FIG. 6*c*). In the example shown in FIGS. 8 and 9, three connectors 3374 are spaced along each of the first and second portions 3352, 3354 of the tube 3350. In some examples (e.g. as shown in FIGS. 8 and 9) the connectors 3374 of the first portion 3352 of the tube have the same spacing, relative to the closest end of the variable length portion 3356, as the connectors 3347 of the second portion 3354 of the tube. In such examples the length of the tube 3350 can be adjusted without changing the position of the strap engaging portion 3380 relative to the variable length portion 3356.

In examples, the difference in tube lengths between large and medium settings, and between medium and small settings, may be around 30 mm.

In examples, the adjustment member 3370 may be made from a suitable plastics material, for example a thermoset elastomer. Hytrel™, a thermoplastic polyester elastomer made by DuPont, may be one example of a suitable material.

Referring next to FIGS. 10 to 12 in another example, a single adjustment member 3370 may be formed to extend over tubes 3350 on both sides of the patient's head.

In the example shown in these figures, the adjustment member 3370 is configured to form part of the connection between the tube(s) 3350 and the elbow 3610, and may comprise a central portion 3382 which is engageable with the fluid connection opening 3360 and two arms 3384 extending on opposite sides of the central portion 3382, each of which is configured to engage the second portion 3354 of respective tubes 3350. The central portion 3382 may comprise a cylindrical portion 3386 which is received by the fluid connection opening 3360. The outer surface of the cylindrical portion 3386 may be provided with an annular channel 3388 which is engaged by a complementary rib provided to an internal wall of the fluid connection opening 3360, to thereby hold the adjustment member 3370 in engagement with the tube(s) 3350. A bore 3390 extends through the cylindrical portion 3386 to the opposite side 3392 of the adjustment member 3370. The bore 3390 comprises a formation 3394 configured to engage the elbow 3610.

In the example shown in FIGS. 10 and 11, the adjustment member 3370 is not provided with a strap engaging portion 3380. Instead, strap engaging portions 3380 are provided separately to the second portion 3354 of each tube 3350. As shown in FIGS. 12A and 12B, in one example the strap engaging portions 3380 may be slidably connected to the second portion 3354 of the respective tubes 3350 to allow adjustment of the position of the strap engaging portions 3380 along the tube in a longitudinal direction, such that the patient can choose the "height" of the strap engaging portion 3380. In examples, the slidable connection is provided with the detents such that the strap engaging portion 3380 is moveable between discrete positions.

4.3.3.2 Single Sleeve Covers Tubes

Referring next to FIGS. 27-29, other examples of the technology having a single adjustment member 3370 formed to extend over tubes 3350 on both sides of the patient's head are shown. In each of these examples a sleeve 3363 extends over portions of each tube 3350, and around the fluid connection opening 3360. In examples the sleeve 3363 may extend over substantially the entirety of each tube 3350. In examples the sleeve 3363 may also extend partially or fully over the plenum chamber 3200.

In examples, the tubes 3350 may be provided with a variable length portion 3356, as described above with reference to FIGS. 10 and 11. The sleeve portion 3426 which overlies the variable length portion 3356 may be configured to allow a high degree of stretch or extension with relatively little resistance, so that the extensibility of the variable length portion 3356 is not significantly affected by the presence of the sleeve 3363. The remainder of the sleeve 3363 may have relatively low stretch properties so as to remain in a required position relative to the tubes 3350 in use.

4.3.3.3 Adjustment Member with Multiple Attachment Positions

Referring next to FIGS. 13 and 14, in some examples of the invention at least the second portion 3354 of the tube comprises an attachment means 3372 which is attachable to the adjustment member 3370 in a selected one of a plurality of possible positions. In examples, the first portion 3352 of the tube also comprises an attachment means 3372 which is attachable to the adjustment member 3370 in a selected one of a plurality of possible positions. As shown in FIGS. 13 and 14, in one example both the first and second portions 3352, 3354 of the tube comprise such attachment means 3372. In the example shown, the adjustment member 3370 comprises a plurality of apertures 3376 on either side of a central aperture 3376A. By selecting which of the apertures 3376 the attachment means 3372 of each of the first and second portions 3352, 3354 is connected to, the length of the tube 3350 can be adjusted. The example shown in FIGS. 13 and 14, the adjustable length portion 3356 of the tube may be provided with an additional attachment means 3372A for connection to the adjustment member 3370. This may allow the adjustment member 3370 to remain attached to the tube 3350 while adjustments to the length of the tube are being made. The portions 3396 of the adjustment member 3370 on either side of the central portion comprising the central aperture 3376A may be flexible and/or connected to the central portion by respective living hinges 3398.

The additional attachment means 3372A may be provided to a sub-portion 3356A of the variable length portion 3356 of the tube which is substantially invariable in length.

In examples of the invention, such as that shown in FIGS. 8, 13 and 14, the attachment means 3372 are provided to a posterior side of the tube 3350. This may be particularly advantageous in embodiments (such as that shown in FIGS. 13 and 14) in which the adjustment member 3370 is provided with a strap engaging portion 3380, e.g. a loop, eye or slot, for engaging a strap 3310, e.g. a back strap. This configuration may reduce or eliminate the tendency of the back strap to exert a twisting force on the tube. In such examples, the use of the additional attachment means 3372A may also assist in creating a sufficiently secure connection between the adjustment member 3370 and the tube to ensure that the adjustment member 3370 is not pulled away from the tube by the back strap.

Connecting the adjustment member 3370 to the variable length portion 3356 of the tube may also assist in preventing the variable length portion 3356 buckling when under compression (e.g. when adjusted to suit a small sized head).

Referring next to FIGS. 27-27C in particular, in a similar example to that shown in FIGS. 10 and 11, a single adjustment member is 3370 formed to extend over tubes 3350 on both sides of the patient's head.

The second portion of each tube 3350 may be provided with an attachment means, for example a mushroom shaped connector 3374. The connectors 3374 may extend through apertures in the sleeve 3363.

The adjustment member 3370 may be provided with a plurality of apertures 3376 configured to engage the connectors 3374. By selecting which of the apertures 3376 each connector 3374 is connected to, the length of the tubes 3350 can be adjusted.

In examples the adjustment member 3370 may be made from a suitable plastics material, for example a thermoset elastomer (e.g. Hytrel™) which is covered in a textile 3428. In some examples the textile 3428 on the outer surface 3430 of the adjustment member 3470 may comprise apertures corresponding to the apertures 3376 in the inner material, but in other examples, e.g. as shown in FIG. 27, the textile on the outer surface 3430 may not have any apertures provided. This may result in a smoother appearance. Markings may be provided to the exterior surface 3430 to indicate which setting the adjustment member is set to, as described further below.

Referring next to FIGS. 28 and 28A, in a variation of the example shown in FIG. 27, the sleeve 3363 may be provided with a pair of flaps 3432, each flap 3432 configured to overlie a respective one of the arms 3384. The flaps 3432 may be permanently connected to the sleeve 3363 along one edge 3434 and may be releasably connectable to the sleeve 3363 on the opposite edge by a releasable connector 3436, for example a hook and loop fastening system (e.g. Velcro). In this example the adjustment member 3370 need not be covered in a textile.

4.3.3.4 Slider Adjustment

In one form of the technology the adjustment member 3370 is slidably engaged with at least one of the first and second portions 3352, 3354 of the tube. In the embodiment shown in FIGS. 15 to 17 the adjustment member 3370 is slidably engaged with both the first and second portions 3352, 3354 of the tube.

In the embodiment shown, each of the first and second portions 3352, 3354 is provided with an elongate rail portion 3362 which is substantially parallel to the longitudinal axis of the tube 3350. The rail portions 3362 may be provided adjacent the variable length portion 3356 of the tube.

The adjustment member 3370 comprises a rail engaging portion 3400, for example a channel or groove, which, in use, engages the rail(s). The rail engaging portion 3400 may extend along the entire length of the adjustment member 3370, or separate rail engaging portions may provided at opposite ends of the adjustment member 3370. In the example shown the rail portion 3362 has a substantially circular cross-section, although rails with any suitable cross-section may be used.

In examples, the rail engaging portion 3400 is a tight sliding fit on the rail portions 3362. The friction between the rail engaging portion 3400 and the rail portions 3362 may be sufficient to prevent sliding of the first and second tube portions 3352, 3354 under the normal tension forces experienced by the tube during donning, doffing and normal use of the patent interface 3000, but which still allows the patient to slide the first and/or second portions 3352, 3354 of the tube relative to the adjustment member 3370 when the patient wishes to adjust the length of the tube.

In embodiments the force required to slide the first and/or second portions 3352, 3354 of the tube relative to the adjustment member 3370 is substantially constant along the full range of travel of the tube portions 3352, 3354 relative to the adjustment member 3370. However, in other examples the adjustment member 3370 and/or tube portions 3352, 3354 may be provided with a detent mechanism such that the slidable connection resists sliding when in at least one, or more preferably a plurality of positions (e.g. corresponding to adjustment of the tube length to suit large, medium and small head), but allows relatively easier sliding between those positions.

In the example shown in FIGS. 15A-15C, the adjustment member 3370 is free from connection to the variable length portion 3356 of the tube. However, in the example shown in FIG. 16, a short length of rail portion or other attachment means 3372 is provided to the variable length portion 3356 of the tube so that this portion can be connected to the adjustment member 3370. As with the example described above with reference to FIGS. 13 and 14, this may prevent buckling of the variable length portion 3356 when compressed.

In some examples the connection between the rail engaging portion 3400 and the rail 3362 is configured to resist bending of the tube 3350 adjacent the connection between the adjustment member 3370 and the first and/or second portion 3352, 3354 of the tube. By contrast, in examples of the invention where the attachment means 3372 comprises a laterally projecting portion having a circular cross-section, the respective tube portion may tend to pivot about the attachment means 3372 relative to the adjustment member 3370, particularly if the adjustment member 3370 comprises a strap engaging portion 3380 and has a force in the posterior direction exerted on it by a strap 3310 (e.g. a back strap).

In examples, the first and/or second portion 3352, 3354 of the tube may be provided with markings which indicate the setting (small medium or large) of the adjustment member 3370. The adjustment member 3370 may be provided with one or more suitable markings 3402 (e.g. a pointer) which point to the relevant markings 3366 on the tubes.

4.3.3.5 Sleeve Provided with Adjustment

Referring next to FIGS. 29-29B, in a similar example to that shown in FIGS. 10, 11 and 27, a single adjustment member is 3370 formed to extend over tubes 3350 on both sides of the patient's head.

In this example each adjustment member arm 3384 is provided with a single attachment means, e.g. a connector 3374 or a detent button or projection 3414.

As shown in FIGS. 29 and 29A, the sleeve 3363 comprises a textile pocket 3438, preferably provided to a superior portion of the sleeve 3363 near the fluid connection opening 3360. Each pocket 3484 is provided a plurality of apertures 3376 configured to engage a respective detent button or projection 3414. A reinforcing portion 3440 may be provided around each aperture 3376. In examples, the reinforcing portion 3340 is formed from a thermoplastic by overmoulding. In some examples separate reinforcing portions 3340 may be provided for each aperture 3376.

In examples, the apertures 3376 in each pocket 3438 are connected by a slot 3442 to guide the connector 3374/detent 3414 between the different apertures 3376 when the patient adjusts the size of the headgear.

4.3.3.6 Variable Length Adjustment Means

Referring next to FIGS. 18-20, in another example the positioning and stabilising structure 3300 comprises an adjustment means 3404 comprising a first adjustment means member 3406 which is slidably connectable to a second adjustment means member 3408. In the example shown in the figures, the first adjustment means member 3406 comprises two substantially parallel leg portions 3410. The second adjustment means member 3408 also comprises two substantially parallel leg portions 3412, these being shaped and configured to receive the leg portions 3410 of the first adjustment means member 3406. In the example shown, the leg portions 3412 of the second adjustment means member 3408 are hollow so that the leg portions 3410 of the first adjustment means member 3406 can be received within the hollow portions of the legs of the second adjustment means member 3408.

In use, the first adjustment means member 3406 is connected to the first portion 3352 of the tube and the second adjustment means member 3408 is connected to the second portion 3354 of the tube. As with the example described above with reference to FIGS. 15 and 16, the first and second adjustment means members 3406, 3408 may be configured such that the friction between the legs of the first and second adjustment means members 3406, 3408 is sufficient to prevent sliding of the adjustment means members 3406, 3408 under the normal tension forces experienced by the tube during donning, doffing and normal use of the patent interface, but which still allows the patient to slide the adjustment means members 3406, 3408 relative to each other when the patient wishes to adjust the length of the tube. Alternatively, a detent system may be provided. In the embodiment shown in the FIGS. 18-20, the legs 3410 of the first adjustment means member 3406 are each provided with a detent button or projection 3414 which releasably engages suitable detent apertures, recesses or notches 3416 spaced along the second attachment means member 3408. The detent apertures 3416 may be spaced apart such that the change in length of the adjustment means 3404 corresponds to the required change in length of the tube 3350 to suit small, medium and large size heads.

In the example shown in FIGS. 19 and 20, strap engaging portions 3380 are provided to the tube 3350, rather than to the adjustment means 3404. The adjustment means 3404 may be located such that the strap engaging portions 3380 project through the space between the spaced apart leg portions 3410, 3412 of the first and second attachment means members 3406, 3408. This arrangement means that the adjustment means 3404 does not need to transfer the force from the strap to the tube. The strap engaging portion 3380 may be provided to a posterior side of the tube 3350, to prevent or reduce twisting of the tube due to forces from the strap.

In the example shown in FIGS. 18-20, the first adjustment means member 3406 is provided with markings 3418 which indicate the setting of the adjustment means (e.g. “S” to indicate “small”, “M” to indicate “medium” and “L” to indicate “large”). The markings 3418 are arranged such that the relevant marking 3418 is viewable through an aperture 3420 provided in the second adjustment means member 3408. Additionally, or alternatively, in examples markings 3422 may be provided adjacent the detent apertures 3416 to indicate the setting of the adjustment means, the relevant marking being indicated by the presence of the detent button 3414.

4.3.3.7 System with Multiple Adjustment Means

In some forms of the technology a system for positioning and stabilising a patient interface comprises a positioning and stabilising structure 3300. As previously described, the positioning and stabilising structure 3300 comprises at least one gas delivery tube 3350 which comprises a first portion 3352, a second portion 3354 and a variable length portion 3356 which extends between the first and second portions 3352, 3354. The variable length portion 3356 may be extendable, compressible, or both extendable and compressible from its “at rest” or natural length. In examples, the variable length portion 3356 comprises a corrugated or concertina portion. Varying the length of the variable length portion 3356 has the effect of varying the total length of the gas delivery tube 3350.

Referring next to FIGS. 21 to 23, the system may further comprise a plurality of adjustment members 3370 which are attachable to the first and second tube portions 3352, 3354. The adjustment members 3370 may be of different lengths, such that the length of the tube can be selected by connection of a suitable attachment member 3370 to the first and second portions 3352, 3354 of the tube.

In the example shown in FIGS. 21 to 23, the tube is substantially D shaped in cross-section, with the flat side 3367 of the tube configured to rest against the patient’s head, in use. The flat sides 3367 of the first and second portions 3352, 3354 of the tube comprise recessed portions 3368 immediately adjacent the variable length portion 3356 of the tube.

The variable length portion 3356 of the tube is configured such that it does not extend beyond of the plane of the recessed portions 3368 of the first and second portions 3352, 3354 of the tube. Attachment means 3372 are provided to each of the recessed portions 3368, the attachment means 3372 configured to engage suitable recesses and/or apertures 3376 in the adjustment member 3370.

Each adjustment member 3370 is configured to have substantially the same thickness as the depth of the recessed portions 3368. The adjustment members 3370 are shaped such that when engaged with the tube 3350, a patient facing side of the adjustment member 3370 is substantially co-planar with the flat side 3367 of the tube. The attachment means 3372 are configured so as to substantially not protrude beyond the patient side of the adjustment member 3370.

In some examples each adjustment member 3370 may be provided with a strap engaging portion 3380. In examples, the adjustment member 3370 is a substantially flat, thin member, and the strap engaging portion 3380 is provided substantially in-plane with the remainder of the member. Because the adjustment member 3370 is configured to be in contact with the patient’s head, in use, the force exerted by a strap (e.g. a back strap) on the strap engaging portion 3380 will not exert a twisting force about the central axis of the tube 3350.

In some examples (e.g. as shown in FIGS. 21-25) the attachment means 3372 have a non-circular cross-section.

This may assist in preventing or resist bending of the tube adjacent the connection between the adjustment member 3370 and the first and/or second portion of the tube, as described above with reference to examples which use a sliding mechanism. In the examples shown in FIGS. 21-25 the attachment means 3372 has a substantially rectangular cross-section. However, other cross-sections may also be suitable for resisting such twisting or bending, for example oval, or square.

In the examples shown in FIG. 23, the strap engaging portion 3380 is positioned substantially centrally along the length of the adjustment member 3370. However, in other examples, for example that shown in FIG. 24, the strap engaging portion 3380 may be provided away from the centre of the adjustment member 3370, for example at or towards one end of the adjustment member 3370. In such examples, the adjustment member 3370 may be configured to be attachable to the tube with the strap engaging portion 3380 in a superior position (e.g. as shown in FIG. 25A) or an inferior position (e.g. as shown in FIG. 25B, depending on the patient's requirements or preference. In examples, the adjustment members 3370 are configured to be usable on the tubes on either side of the patient's head (e.g. each adjustment member 3370 is not limited to use on one specific side of the patient's head).

Referring next to FIGS. 30-30C, in a variation of the example shown in FIGS. 21-23, each tube 3350 may be provided with a sleeve 3363, or a single sleeve may cover both tubes 3350. The sleeve portion 3426 which covers the variable length portion 3356 may be configured to allow a high degree of stretch or extension with relatively little resistance, so that the extensibility of the variable length portion is not significantly affected by the presence of the sleeve 3350.

As shown in FIG. 30A, the attachment means 3372, e.g. connectors 3374, extend through apertures in the sleeve 3350.

In examples the adjustment members 3370 may be covered with a textile 3428. In examples, apertures 3376 extend through the adjustment member in a similar configuration to that shown in FIGS. 21-23. However, as shown in FIG. 30C (which shows a cross-section through the adjustment member) in another example apertures 3376 (e.g. blind apertures 3377) are provided in a boss provided to an inner face of the adjustment members.

In the example shown in FIG. 26, each of the adjustment members 3370 are configured to engage a posterior of the tube 3350. As with the examples described above, each adjustment member 3370 may be provided with a strap engaging portion 3380. The strap engaging portion 3380 may be provided at the centre of the adjustment member 3370 or away from the centre of the adjustment member 3370, for example at or towards one end of the adjustment member 3370.

As well as allowing for adjustment of the tube length to suit different size heads, the systems described above may be provided with adjustment means which have a length and/or a configuration (or position) of the strap engaging portion 3380 which make the positioning and stabilising structure suitable for use with different types of mask, for example full face, nasal etc.

In another example, a positioning and stabilising structure 3300 may be provided with only a single adjustment member 3370, for example one similar to any one of those described above with reference to FIG. 5, 8, 9, 13, 23, 24 or 26. This may allow adjustment of the positioning and stabilising structure between a first configuration in which the adjustment member 3370 is either not connected to the tube at all, or is connected to only one of the first and second tube portions 3352, 3354, (e.g. for use with large heads) and a second configuration in which the adjustment member 3370 is connected to both the first and second portions 3352, 3354 of the tube, thereby compressing the variable length portion (e.g. for use with smaller heads). In such examples the strap engaging portion may be provided directly to the tube (e.g. as shown in FIG. 12), rather than to the adjustment member 3370.

The adjustment members described above with reference to FIGS. 21-26 may be made from a rigid material such as polycarbonate, or less rigid material such as Hytrel™ or a very stiff silicone (for example, around 80 shore). If a hard plastic is used it may be skinned over with a softer silicone or thermoplastic elastomer.

In examples the adjustment members 3370 may be configured to allow the tube lengths to be varied in steps of substantially 30 mm.

4.3.4 Vent

In one form, the patient interface 3000 includes a vent 3500 constructed and arranged to allow for the washout of exhaled gases, e.g. carbon dioxide.

In certain forms the vent 3500 is configured to allow a continuous vent flow from an interior of the plenum chamber 3200 to ambient whilst the pressure within the plenum chamber is positive with respect to ambient. The vent 3500 is configured such that the vent flow rate has a magnitude sufficient to reduce rebreathing of exhaled $CO_2$ by the patient while maintaining the therapeutic pressure in the plenum chamber in use.

One form of vent 3500 in accordance with the present technology comprises a plurality of holes, for example, about 20 to about 80 holes, or about 40 to about 60 holes, or about 45 to about 55 holes.

The vent 3500 may be located in the plenum chamber 3200. Alternatively, the vent 3500 is located in a decoupling structure, e.g., a swivel.

4.3.5 Decoupling Structure(s)

In one form the patient interface 3000 includes at least one decoupling structure, for example, a swivel or a ball and socket.

4.3.6 Connection Port

Connection port 3600 allows for connection to the air circuit 4170.

4.3.7 Forehead Support

In one form, the patient interface 3000 includes a forehead support 3700.

4.3.8 Anti-Asphyxia Valve

In one form, the patient interface 3000 includes an anti-asphyxia valve.

4.3.9 Ports

In one form of the present technology, a patient interface 3000 includes one or more ports that allow access to the volume within the plenum chamber 3200. In one form this allows a clinician to supply supplementary oxygen. In one form, this allows for the direct measurement of a property of gases within the plenum chamber 3200, such as the pressure.

4.4 RPT Device

An RPT device 4000 in accordance with one aspect of the present technology comprises mechanical, pneumatic, and/or electrical components and is configured to execute one or more algorithms, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH2O, or at least 10cmH2O, or at least 20 cmH2O.

Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of a pneumatic block of the RPT device and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller. One example of an air circuit 4170 comprising a heated wire circuit is described in U.S. Pat. No. 8,733,349, which is incorporated herewithin in its entirety by reference.

4.5 Humidifier

4.5.1 Humidifier Overview

In one form of the present technology there is provided a humidifier 5000 to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir, a humidifier inlet to receive a flow of air, and a humidifier outlet to deliver a humidified flow of air.

4.6 Respiratory Therapy Modes

Various respiratory therapy modes may be implemented by the disclosed respiratory therapy system, including CPAP and bi-level therapy.

4.7 Glossary

For the purposes of the present technology disclosure, in certain forms of the present technology, one or more of the following definitions may apply. In other forms of the present technology, alternative definitions may apply.

4.7.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Device flow rate, Qd, is the flow rate of air leaving the RPT device. Total flow rate, Qt, is the flow rate of air and any supplementary gas reaching the patient interface via the air circuit. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Flow therapy: Respiratory therapy comprising the delivery of a flow of air to an entrance to the airways at a controlled flow rate referred to as the treatment flow rate that is typically positive throughout the patient's breathing cycle.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including cmH2O, g-f/cm$^2$ and hectopascal. 1 cmH2O is equal to 1 g-f/cm$^2$ and is approximately 0.98 hectopascal (1 hectopascal=100 Pa=100 N/m$^2$=1 millibar 0.001 atm). In this specification, unless otherwise stated, pressure is given in units of cmH2O.

The pressure in the patient interface is given the symbol Pm, while the treatment pressure, which represents a target value to be achieved by the interface pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

4.7.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

4.7.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

- 'Soft' materials may include silicone or thermo-plastic elastomer (TPE), and may, e.g. readily deform under finger pressure.
- 'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions. The inverse of stiffness is flexibility.

Floppy structure or component. A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 cmH2O pressure.

As an example, an I-beam may comprise a different bending stiffness (resistance to a bending load) in a first direction in comparison to a second, orthogonal direction. In another example, a structure or component may be floppy in a first direction and rigid in a second direction.

4.7.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

- (i) Flattened: Having a rise followed by a relatively flat portion, followed by a fall.
- (ii) M-shaped: Having two local peaks, one at the leading edge, and one at the trailing edge, and a relatively flat portion between the two peaks.
- (iii) Chair-shaped: Having a single local peak, the peak being at the leading edge, followed by a relatively flat portion.
- (iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

- (i) a 30% reduction in patient breathing for at least one0 seconds plus an associated 4% desaturation; or (ii) a reduction in patient breathing (but less than 50%) for at least one0 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

4.7.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired interface pressure which the ventilator will attempt to achieve at a given time.

End expiratory pressure (EEP): Desired interface pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired interface pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

4.7.4 Anatomy 4.7.4.1 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius):

Lip, upper (labrale superius):

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion 4.7.4.2 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

4.7.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

4.7.5 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

4.7.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

4.7.6.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

4.7.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

4.7.6.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

4.7.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

4.8 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

4.9 Reference Signs List

| | |
|---|---|
| patient | 1000 |
| bed partner | 1100 |
| patient interface | 3000 |
| seal forming structure | 3100 |
| plenum chamber | 3200 |
| chord | 3210 |
| superior point | 3220 |
| inferior point | 3230 |
| positioning and stabilising structure | 3300 |
| strap | 3310 |
| tab | 3320 |
| gas delivery tube | 3350 |
| first portion | 3352 |
| second portion | 3354 |
| variable length portion | 3356 |
| corrugated portion | 3358 |
| fluid connection opening | 3360 |
| rail portion | 3362 |
| sleeve | 3363 |
| rail engaging portion | 3364 |
| markings | 3366 |
| flat side | 3367 |
| recessed portion | 3368 |
| adjustment member | 3370 |
| attachment means | 3372 |
| additional attachment means | 3372A |
| connectors | 3374 |
| aperture | 3376 |
| central aperture | 3376A |
| blind aperture | 3377 |
| rib | 3378 |
| strap engaging portion | 3380 |
| central portion | 3382 |
| arms | 3384 |
| cylindrical portion | 3386 |
| annular channel | 3388 |
| bore | 3390 |
| opposite side | 3392 |
| formation | 3394 |
| portions | 3396 |
| living hinge | 3398 |
| rail engaging portion | 3400 |
| markings | 3402 |
| adjustment means | 3404 |
| adjustment means member | 3406 |
| adjustment means member | 3408 |
| leg portion | 3410 |
| leg portion | 3412 |
| detent button | 3414 |
| detent aperture | 3416 |
| aperture | 3418 |
| markings | 3420 |
| markings | 3422 |
| portion of sleeve | 3426 |
| textile | 3428 |
| outer surface | 3430 |
| flap | 3432 |
| edge | 3434 |
| releasable connector | 3436 |
| pocket | 3438 |
| reinforcing portion | 3440 |
| slot | 3442 |
| boss | 3444 |
| vent | 3500 |
| connection port | 3600 |
| elbow | 3610 |

-continued

| | |
|---|---|
| forehead support | 3700 |
| RPT device | 4000 |
| air circuit | 4170 |
| humidifier | 5000 |

The invention claimed is:

1. A positioning and stabilising structure to provide a force to hold a seal-forming structure in a therapeutically effective position on a patient's head, the seal-forming structure constructed and arranged to form a seal with a region of the patient's face surrounding an entrance to the patient's airways for sealed delivery of a flow of air at a therapeutic pressure of at least 6 cmH2O above ambient air pressure to at least the patient's nares throughout the patient's respiratory cycle in use, the positioning and stabilising structure comprising:

a gas delivery tube to receive the flow of air from a connection port on top of the patient's head and to deliver the flow of air to the entrance of the patient's airways via the seal-forming structure, the gas delivery tube being constructed and arranged to contact, in use, at least a region of the patient's head superior to an otobasion superior of the patient's head, the gas delivery tube further comprising a first portion, a second portion, and a variable length portion between the first and second portions which is extendible and/or compressible, the variable length portion being integrally formed with the first and second portions, wherein a plurality of spaced apart attachment means protrude from a surface of the second portion, the positioning and stabilising structure further comprising an adjustment member which is attached or attachable to the first portion of the gas delivery tube and is attachable to the second portion of the gas delivery tube at a selected one of the attachment means to thereby adjust the length of the variable length portion; and wherein the adjustment member is provided with a strap engaging portion.

2. The positioning and stabilizing structure of claim 1 wherein each attachment means comprises a projecting portion adapted to engage an aperture in the adjustment member.

3. The positioning and stabilising structure of claim 2 wherein the attachment means comprise mushroom connectors.

4. The positioning and stabilising structure of claim 1, wherein an aperture is provided at each end of the adjustment member.

5. The positioning and stabilising structure of claim 1 wherein the strap engaging portion is located substantially centrally along the length of the adjustment member.

6. The positioning and stabilising structure of claim 1 wherein the strap engaging portion is located at one end of the adjustment member.

7. The positioning and stabilising structure of claim 1, wherein a plurality of second spaced apart attachment means protrude from a surface of the first portion, wherein the adjustment member is attachable to a selected one of the second attachment means.

8. The positioning and stabilising structure of claim 1, wherein the adjustment member extends, in use, over the top of the patient's head.

9. The positioning and stabilising structure of claim 8, comprising a second gas delivery tube, the second gas delivery tube comprising a first portion, a second portion, and a variable length portion between the first and second portions which is extendible and/or compressible, wherein a plurality of spaced apart attachment means protrude from a surface of the second portion of the second gas delivery tube, wherein the adjustment member is attachable to the attachment means of both gas delivery tubes.

10. The positioning and stabilising structure of claim 9 wherein the positioning and stabilising structure comprises a fluid connection opening and the adjustment member comprises a cylindrical portion which engages the opening, wherein a bore extends through the cylindrical portion to the opposite side of the attachment member.

11. The positioning and stabilising structure of claim 10 wherein the bore comprises a formation configured to engage an elbow.

12. The positioning and stabilising structure of claim 9 wherein strap engaging portions are provided to each gas delivery tube.

13. The positioning and stabilising structure of claim 12 wherein each strap engaging portion is slideable relative to the gas delivery tube to which it is provided.

14. A positioning and stabilising structure to provide a force to hold a seal-forming structure in a therapeutically effective position on a patient's head, the seal-forming structure constructed and arranged to form a seal with a region of the patient's face surrounding an entrance to the patient's airways for sealed delivery of a flow of air at a therapeutic pressure of at least 6 cmH2O above ambient air pressure to at least the patient's nares throughout the patient's respiratory cycle in use, the positioning and stabilising structure comprising: a gas delivery tube to receive the flow of air from a connection port on top of the patient's head and to deliver the flow of air to the entrance of the patient's airways via the seal-forming structure, the gas delivery tube being constructed and arranged to contact, in use, at least a region of the patient's head superior to an otobasion superior of the patient's head, the gas delivery tube further comprising a first portion, a second portion, and a variable length portion between the first and second portions which is extendible and/or compressible, the second portion comprising a rib extending from a posterior surface thereof, wherein a plurality of spaced apart attachment means project from a surface of the rib, the positioning and stabilising structure further comprising an adjustment member which is attached or attachable to the first portion of the gas delivery tube and is attached or attachable to a selected one of the attachment means to thereby adjust the length of the variable length portion.

15. The positioning and stabilising structure of claim 14 wherein the attachment means extend laterally from a lateral surface of the rib.

16. The positioning and stabilising structure of claim 14 wherein the adjustment member is provided with a strap engaging portion.

17. The positioning and stabilising structure of claim 14 wherein the first portion comprises a second rib extending from a posterior surface thereof, wherein the adjustment member is attached or attachable to the second rib.

18. The positioning and stabilising structure of claim 17, wherein a plurality of second spaced apart attachment means protrude from a surface of the second rib, wherein the adjustment member is attachable to a selected one of the second attachment means.

* * * * *